US007576189B2

(12) United States Patent
Rosen et al.

(10) Patent No.: US 7,576,189 B2
(45) Date of Patent: Aug. 18, 2009

(54) ANTIBODIES TO HUMAN VASCULAR ENDOTHELIAL GROWTH FACTOR 2 AND METHODS OF USING THE SAME

(75) Inventors: Craig A. Rosen, Laytonsville, MD (US); Jing-Shan Hu, Mountain View, CA (US); Liang Cao, Bethesda, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 53 days.

(21) Appl. No.: 11/211,724

(22) Filed: Aug. 26, 2005

(65) Prior Publication Data

US 2005/0287143 A1 Dec. 29, 2005

Related U.S. Application Data

(60) Continuation of application No. 10/023,584, filed on Dec. 21, 2001, now Pat. No. 7,109,308, which is a division of application No. 08/465,968, filed on Jun. 6, 1995, now Pat. No. 6,608,182, which is a continuation-in-part of application No. 08/207,550, filed on Mar. 8, 1994, now abandoned.

(51) Int. Cl.
*C07K 16/00* (2006.01)
*C12P 21/08* (2006.01)
*G01N 33/53* (2006.01)
*A61K 39/395* (2006.01)
*A61K 39/00* (2006.01)

(52) U.S. Cl. ............. 530/389.2; 530/387.1; 530/387.3; 530/388.1; 530/388.15; 530/389.1; 530/391.3; 435/7.1; 424/130.1; 424/133.1; 424/139.1

(58) Field of Classification Search ........................ None
See application file for complete search history.

(56) References Cited

U.S. PATENT DOCUMENTS

| | | | |
|---|---|---|---|
| 5,073,492 A | 12/1991 | Chen et al. | |
| 5,194,596 A | 3/1993 | Tischer et al. | |
| 5,219,739 A | 6/1993 | Tischer et al. | |
| 5,234,908 A | 8/1993 | Szabo et al. | |
| 5,240,848 A | 8/1993 | Keck et al. | |
| 5,283,354 A | 2/1994 | Lemischka | |
| 5,326,695 A | 7/1994 | Andersson et al. | |
| 5,607,918 A | 3/1997 | Eriksson et al. | |
| 5,633,147 A | 5/1997 | Meissner et al. | |
| 5,652,225 A | 7/1997 | Isner | |
| 5,661,133 A | 8/1997 | Leiden et al. | |
| 5,693,622 A | 12/1997 | Wolff et al. | |
| 5,776,755 A | 7/1998 | Alitalo et al. | |
| 5,792,453 A | 8/1998 | Hammond et al. | |
| 5,840,693 A | 11/1998 | Eriksson et al. | |
| 5,861,301 A | 1/1999 | Terman et al. | |
| 5,932,540 A | 8/1999 | Hu et al. | |
| 5,935,820 A | 8/1999 | Hu et al. | |
| 6,040,157 A | 3/2000 | Hu et al. | |
| 6,121,246 A | 9/2000 | Isner | |
| 6,130,071 A | 10/2000 | Alitalo et al. | |
| 6,221,839 B1 | 4/2001 | Alitalo et al. | |
| 6,245,530 B1 | 6/2001 | Alitalo et al. | |
| 6,361,946 B1 | 3/2002 | Alitalo et al. | |
| 6,403,088 B1 | 6/2002 | Alitalo et al. | |
| 6,451,764 B1 | 9/2002 | Lee et al. | |
| 6,608,182 B1 | 8/2003 | Rosen et al. | |
| 6,645,933 B1 | 11/2003 | Alitalo et al. | |
| 6,734,285 B2 | 5/2004 | Hu et al. | |
| 6,824,777 B1 | 11/2004 | Alitalo et al. | |
| 6,884,879 B1 | 4/2005 | Baca et al. | |
| 7,109,308 B1 | 9/2006 | Rosen et al. | |
| 7,115,392 B2 | 10/2006 | Rosen et al. | |
| 7,153,827 B1 | 12/2006 | Hu et al. | |
| 7,153,942 B2 | 12/2006 | Hu et al. | |
| 7,186,688 B1 | 3/2007 | Hu et al. | |
| 7,208,582 B2 | 4/2007 | Rosen et al. | |
| 7,223,724 B1 | 5/2007 | Alderson et al. | |
| 7,227,005 B1 | 6/2007 | Hu et al. | |
| 7,273,751 B2 | 9/2007 | Coleman | |
| 7,402,312 B2 | 7/2008 | Rosen et al. | |
| 7,439,333 B2 | 10/2008 | Hu et al. | |
| 2003/0215921 A1 | 11/2003 | Coleman | |
| 2004/0214286 A1 | 10/2004 | Hu et al. | |
| 2005/0059117 A1 | 3/2005 | Rosen et al. | |
| 2005/0176103 A1 | 8/2005 | Hu et al. | |
| 2005/0181979 A1 | 8/2005 | Alderson et al. | |
| 2005/0192429 A1 | 9/2005 | Rosen et al. | |
| 2005/0232921 A1 | 10/2005 | Rosen et al. | |
| 2006/0014252 A1 | 1/2006 | Lyman | |
| 2006/0025331 A1 | 2/2006 | Hu et al. | |
| 2006/0057117 A1 | 3/2006 | Coleman | |

FOREIGN PATENT DOCUMENTS

AU 710696 9/1999

(Continued)

OTHER PUBLICATIONS

U.S. Appl. No. 09/257,272, inventors Hu et al., filed Feb. 25, 1999 (Not Published).

(Continued)

*Primary Examiner*—Robert Landsman
(74) *Attorney, Agent, or Firm*—Sterne, Kessler, Goldstein & Fox P.L.L.C.

(57) ABSTRACT

Disclosed is a human VEGF2 polypeptide and DNA(RNA) encoding such VEGF2 polypeptides. Also provided is a procedure for producing such polypeptide by recombinant techniques and antibodies and antagonist against such polypeptide. Also disclosed is a method of using such polypeptide for stimulating wound healing and for vascular tissue repair. Also provided are methods of using the antagonists to inhibit tumor growth, inflammation and to treat diabetic retinopathy, rheumatoid arthritis and psoriasis. Diagnostic methods for detecting mutations in the VEGF2 coding sequence and alterations in the concentration of VEGF2 protein in a sample derived from a host are also disclosed.

48 Claims, 14 Drawing Sheets

FOREIGN PATENT DOCUMENTS

| | | |
|---|---|---|
| EP | 0186084 A2 | 7/1986 |
| EP | 0399816 A1 | 11/1990 |
| EP | 0476983 | 3/1992 |
| EP | 0506477 | 9/1992 |
| JP | 64-38100 A | 2/1989 |
| JP | 2-117698 A | 5/1990 |
| WO | WO 91/02058 | 2/1991 |
| WO | WO 92/14748 | 9/1992 |
| WO | WO 94/11506 A1 | 5/1994 |
| WO | WO 95/19985 | 7/1995 |
| WO | WO 95/24414 | 9/1995 |
| WO | WO 95/24473 | 12/1995 |
| WO | WO 96/05856 | 2/1996 |
| WO | WO 96/39515 | 12/1996 |
| WO | WO 97/00271 | 1/1997 |
| WO | WO 97/05250 | 2/1997 |
| WO | WO 97/08320 | 3/1997 |
| WO | WO 97/09427 | 3/1997 |
| WO | WO 97/17442 | 5/1997 |
| WO | WO 97/19694 | 6/1997 |
| WO | WO 98/06844 | 2/1998 |
| WO | WO 98/07832 | 2/1998 |
| WO | WO 98/24811 | 6/1998 |
| WO | WO 98/33917 | 6/1998 |
| WO | WO 98/39035 | 9/1998 |
| WO | WO 98/49300 | 11/1998 |
| WO | WO 98/55619 | 12/1998 |
| WO | WO 98/56936 | 12/1998 |
| WO | WO 99/02545 | 1/1999 |
| WO | WO 99/08522 | 2/1999 |
| WO | WO 99/20749 | 4/1999 |
| WO | WO 99/21590 | 5/1999 |
| WO | WO 99/46364 | 9/1999 |
| WO | WO 00/45835 A1 | 8/2000 |
| WO | WO 00/73430 | 12/2000 |
| WO | WO 00/75163 | 12/2000 |
| WO | WO 01/57226 A1 | 8/2001 |
| WO | WO 01/58956 | 8/2001 |
| WO | WO 02/11769 A1 | 2/2002 |
| WO | WO 02/083704 A1 | 10/2002 |
| WO | WO 02/083849 A2 | 10/2002 |
| WO | WO 02/083850 A2 | 10/2002 |
| WO | WO 03/097660 A1 | 11/2003 |
| ZA | 9-403464 | 1/1996 |

OTHER PUBLICATIONS

U.S. Appl. No. 09/499,468, inventors Alderson et al., filed Feb. 7, 2000 (Not Published).

U.S. Appl. No. 11/730,696, inventors Rosen et al., filed Apr. 3, 2007 (Not Published).

Dermer, G.B., "Another Anniversary for the War on Cancer," *Bio/Technol.* 12:320, Wiley-VCH Verlag GmbH & Co. (Mar. 1994).

Duda, D.G., et al., "VEGF-targeted cancer therapy strategies: current progress, hurdles and future prospects," *Trends Molec. Med.* 13(6):223-230, Elsevier Ltd. (Apr. 2007).

Gura, T., "Systems for Identifying New Drugs Are Ofter Faulty," *Science* 278(5340):1041-1042, American Association for the Advancement of Science (Nov. 1997).

Landolfi, N.F., et al., "The Integrity of the Ball-and-Socket Joint Between V and C Domains Is Essential for Complete Activity of a Humanized Antibody," *J. Immunol.* 166:1748-1754, The American Association of Immunologists (Feb. 2001).

Liu, Z., et al., "Fine mapping of the antigen-antibody interaction of scFv215, a recombinant antibody inhibiting RNA polymerase II ffrom *Drosophila melanogaster*," *J. Mol. Recognit.* 12:103-111, John Wiley & Sons, Ltd. (Mar. 1999).

Achen et al., "Vascular endothelial growth factor D (VEGF-D) is a ligand for the tyrosine kinases VEGF receptor-2 (Flk1) and VEGF receptor 3 (Flt4)," *Proc. Natl. Acad. Sci.* (USA) 95:548-553, National Academy of Sciences (Jan. 1998).

Alderson et al., "Vascular endothelial cell growth factor (VEGF)-2 enhances the development of rat photoreceptor cells in vitro," *Keystone Symposia, Ocular Cell and Molec. Bio.* 202 (1999).

Altshuler et al., "Taurine promotes the differentiation of a vertebrate retinal cell type in vitro," *Development I 19*:1317-1328, Company of Biologists Limited (Dec. 1993).

Andersson et al., "Assignment of interchain disulfide bonds in platelet-derived growth factor (PDFG) as evidence for agonist activity of monomeric PDGF," *J. Bio. Chem.* 267:11260-11266, American Society for Biochemistry and Molecular Biology (1992).

Andersson, W.F. "Human gene therapy," *Science* 256:808-813, American Association for the Advancement of Science (1992).

Aprelikova et al., "FLT4, a novel class III receptor tyrosine kinase in chromosome 5q33-qter," *Cancer Res.* 52:746-748, American Association for Cancer Research (1992).

Bell et al., "Human epidermanl growth factor precursor: cDNA sequence, expression in vitro and gene organization," *Nucl. Acids Res.* 14:8427-8446, Oxford University Press (1986).

Bellomo et al., "Mice Lacking the Vascular Endothelial Growth Factor-B Gene (Vegfb) Have Smaller Hearts, Dysfunctional Coronary Vasculature, and Impaired Recovery From Cardiac Ishemia," *Circ. Research* 86:e29-e35, Lippincott, Williams & Wilkins (Feb. 2000).

Berse et al., "Vascular permeability factor (vacular endothelial growth factor) gene is expressed differentially in normal tissues, macrophages, and tumors," *Mol. Biol. Cell.* 3:211-220, American Society for Cell Biology (1992).

Betsholtz et al., "cDNA sequence and chromosomal localization of human platelet-derived growth factor A-chain and its expression in tumor cell lines," *Nature* 320:695-699, Macmillan Publishers (1986).

Bocker-Meffert et al., "Erythropoietin and VEGF Promote Neural Outgrowth from Retinal Explants in Postnatal Rats," *Invest. Opthalmol. Vis. Sci.* 43:2021-2026, Association for Research in Vision and Opthalmology (Jun. 2002).

Brier et al., "Expression of vascular endothelial growth factor during embryonic angiogenesis and endothelial cell differentiation," *Development* 114:521-532 (1992).

Claffey et al., "Vascular endothelial growth factor," *J. Biol. Chem.* 267:16317-16322 (1992).

Cockerill et al., "Angiogenesis: Models and Modulators," *Intl. Rev. Cytology* 159:113-160 (1995).

Corson et al., "Fibrillin binds calcium and is coded by cDNAs that reveal a multidomain structure and alternatively spliced exons at the 5' end," *Genomics* 17:476-484 (Aug. 1993).

Dignam et al., "Balbiani ring 3 in chironomus tentans encodes a 185-kDa secretory protein which is synthesized throughout the fourth larval instar," *Gene* 88:133-140 (1990).

Eichmann et al., "Avian VEGF-C: cloning, embryonic expression pattern and stimulation of the differentiation of VEGFR2-expressing endothelial cell precursor," *Development* 125:743-752 (Feb. 1998).

Ferrara et al., "Molecular and biological properties of the vascular endothelial growth factor family of proteins," *Endocrine Rev.* 13:18-32 (1992).

Ferrara et al., "The vascular endothelial growth factor family of polypeptides," *J. Cell. Bio.* 47:211-218 (1991).

Finnerty et al., "Molecular cloning of murine FLT and FLT4," *Oncogene* 8:2293-2298 (Aug. 1993).

Friedman, T., "A brief history of gene therapy," *Nat. Genetics* 2:93-98 (1992).

Seigel, G.M., "The golden age of retinal cell culture," *Molec. Vis.* 5:4 (Apr. 1999).

Gamble et al., "Regulation of In Vitro Capillary TubeFormation by Anti-Integrin Anbodies," *J. Cell. Bio.* 121:931-943 (May 1993).

George et al., "Current Methods in Sequence Comparison and Analysis," Macromolecular Seq. and Syn. Selected Meth—Application (Alan R. Liss), pp. 127-149 (1988).

Gerhardinger et al., "Expression of Vascular Endothelial Growth Factor in the Human Retina and in Nonproliferative Diabetic Retinopathy," *Am. J. Pathol.* 152:1453-1462 (Jun. 1998).

Goldspiel et al., "Human Gene Therapy," *Clin. Pharm.* 12:488-505 (Jul. 1993).

Grimmond et al., "Cloning and Characterization of a Novel Human Gene Related to Vascular Endothelial Growth Factor," *Genome Res.* 6:124-131 (Feb. 1996).

Guzman et al., "Efficient gene transfer into myocardium by direct injection of adenovirus vectors," *Circ. Res.* 73:1202-1207 (Dec. 1993).

Hannink et al., "Deletions in the C-Terminal Coding Region of the v-sis Gene: Dimerization Is Required for Transmission," *Mol. Cell. Biol.* 1304-1314 (1986).

Hirai et al., "Expression of Vascular Endothelial Growth Factors (VEGF-A/VEGF-1 and VEGF-C/VEGF-2) in Postmenopausal Uterine Endometrial Carcinoma," *Gynecol. Oncol.* 80:181-188 (Feb. 2001).

Heldin et al., "Structure of platelet-derived growth factor: implications for functional properties," *Growth Factors* 8:245-252 (1993).

Hockel et al., "Therapeutic angiogenesis," *Arch. Surg.* 128:423-429 (Apr. 1993).

Hu et al., "A novel regulatory function of proteolytically cleaved VEGF-2 for vascular endothelial smooth muscle cells," *FASEB J.* 11:498-504 (May 1997).

Hyde et al., "Correction of the ion transport defect in cystic fibrosis transfenic mice by gene therapy," *Nature* 362:250-255 (Mar. 1993).

Jukov et al., "A novel vascular endothelial factor, VEGF-C, is a ligand for the Flt4 (VEGFR-3) and KDR (VEGFR-2) receptor tyrosine kinases," *EMBO J.* 15:290-298 (Jan. 1996).

Jukov et al., "Proteolytic processing regulates receptor specificity and activity of VEGF-C," *EMBO J.* 16:3898-3911 (Jul. 1997).

Kaipinen et al., "The related FLT4, FLT1 and KDR receptor tyrosine kinases show distinct expression patterns in human fetal endothelial cells," *J. Exp. Med.* 178:2077-2088 (Dec. 1993).

Kay et al., "In Vivo Gene Therapy of Hemophilia B: Sustained Partial Correction in Factor IX-Deficient Dogs," *Science* 262:117-119 (Oct. 1993).

Keck et al., Vascular permeability factor, an endothelial cell mitogen related to PDGF, *Science* 246:1309 (1989).

Kelley et al., "Regulation of a Proliferation and Photoreceptor Differentiation in Fetal Human Retinal Cell Cultures," *Invest. Ophthalmol. Vis. Sci.* 36:1280-1289 (Jun. 1995).

Kingsley, D. "The TGF-b superfamily: new members, new receptors, and new genetic tests of function in different organisms," *Genes & Dev.* 8:133-146 (Jan. 1994).

Kolodka et al., "Hepatic Gene Therapy: Efficient Retroviral-Mediated Gene Transfer into Rat Hepatocyes in Vivo," *Som. Cell Mol. Gen.* 19:491-497 (Sep. 1993).

Kukk et al., "VEGF-C receptor binding and pattern of expression with VEGFR-3 suggests a role in lymphatic vascular development," *Development* 122:3829-3837 (Dec. 1996).

Lee et al., "Vascular endothelial growth factor-related protein: a ligand and specific activator of the tyrosine kinase receptor Flt4," *Proc. Natl. Acad. Sci. (USA)* 93:1988-1992 (Mar. 1996).

Leung et al., "Vascular endothelial growth factor is a secreted angiogenic mitogen," *Science* 246:1306-1309 (1989).

Litwin et al., "Role of Cytokines in Endothelial Cell Functions," *Human Cytokines* 101-129 (Apr. 1995).

Maglione et al., "Isolation of a human placenta cDNA coding for a protein related to the vascular permeability factor," *Proc. Natl. Acad. Sci. (USA)* 88:9267-9271 (1991).

Maglione et al., "Two alternative mRNAs coding for the angiogenic factor, placenta growth factor (PlGF), are transcribed from a single gene of chromosome 14," *Oncogene* 8:925-931 (1993).

Massague, J. "The transforming growth factor-beta family," *Annu. Rev. Cell Biol.* 6:597-641 (1990).

Matthews et al., "A receptor tyrosine kinase cDNA isolated from a population of enriched primitive hematopoietic cells and exhibiting close genetic linkage to c-kit," *Proc. Natl. Acad. Sci. (USA)* 88:9026-9030 (1991).

Millauer et al., "Glioblastoma growth inhibited in vivo by a dominant-negative Flk-1 mutant," *Nature* 367:576-579 (Feb. 1994).

Millauer et al., "High affinity VEGF binding and development expression suggest FLK-1 as a major regulator of vasculogenesis and angiogenesis," *Cell* 72:835-846 (Mar. 1993).

Ngo et al., "The Protein Folding Problem and Tertiary Structure Prediction," Kenneth Merz, Jr. and Scott LeGrand eds., Birkhauser, Boston, pp. 492-495 (1994).

Oltvai et al., "Bcl-2 heterodimerizes in vivo with a conserved homolog, bax, that accelerates programmed cell death," *Cell* 74:609-619 (Aug. 1993).

Pajusola et al., "FLT4 receptor tyrosine kinase contains seven immunoglobulin-like loops and is expressed in multiple human tissues and cell lines," *Cancer Res.* 52:5738-5743 (1992).

Pajusola et al., "Two human FLT4 receptor tyrosine kinase isoforms with distinct carboxy terminal tails are produced by alternative processing of primary transcripts," *Oncogene* 8:2931-2937 (Nov. 1993).

Paulsson et al., "The balbani ring 3 gene in chironomus tentans has a diverged repetitive structure split by many introns," *J. Mol. Biol.* 211:331-349 (1990).

Rudikoff et al., "Single amino acid substitution altering antigen-binding specificity," *Proc. Natl. Acad. Sci. USA* 79:1979-1983 (1982).

Schratzberger et al., "Reversal of experimental diabetic neuropathy by VEGF gene transfer," *J. Clin. Invest.* 107:1083-1092 (May 2001).

Schulz-Key et al., "Ciliary Neurotrophic Factor as a Transient Negative Regulator of Rod Development in Rat Retina," *Invest. Ophthalmol. Vis. Sci.* 43:3099-3108 (Sep. 2002).

Shibuya et al., "Nucleotide sequence and expression of a novel human receptor-type tyrosine kinase gene (*flt*) closely related to the *fms* family," Oncogene 519-524 (1990).

Silins et al., "Analysis of the Promoter Region of the Human VEGF-Related Factor Gene," *Biochem. Biophys. Res. Comm.* 230:413-418 (Jan. 1997).

Stacker et al., "The Vascular Endothelial Growth Factor Family: Signalling for Vascular Development," *Growth Factors* 17:1-11 (1999).

Stewart et al., "Insulin delivery by somatic cell gene therapy," *J. Mol. Endocrin.* 11:335-341 (Dec. 1993).

Tanaka et al., "DNA sequence encoding the amino-terminal region of the human c-*src* protein: implications of sequence divergence amon *src*-type kinase oncogenes," *Mol. Cell Biol.* 7:1978-1983 (1987).

Terman et al., "Identification of the new endothelial cell growth factor receptor tyrosine kinase," *Oncogene* 6:1677-1683 (1991).

Terman et al., "Identification of the kdr tyrosine kinase as a receptor for vascular endothelial cell growth factor," *Biochem. Biophys. Res. Commun.* 187:1579-1586 (1992).

Tischer et al., "Vascular endothelial growth factor: A new member of the platelet-derived growth factor gene family," *Biochem. Biophys. Res. Commun.* 165:1198-1206 (1989).

Tischer et al., "The Human Gene for Vascular Endothelial Growth Factor," *J. Biol. Chem.* 266:11947-11954 (1991).

Townson et al., "Characterization of the Murine VEGF-Related Factor Gene," *Biochem. Biophys. Res. Commun.* 220:922-928 (Mar. 1996).

Tsujimoto et al., "Analysis of the structure, transcripts, and protein products of *bcl*-2, the gene involved in human follicular lymphoma," *Proc. Natl. Acad. Sci. (USA)* 83:5214-5218 (1986).

Vale et al., "Percutaneous Electromechanical Mapping Demonstrates Efficacy of pVGI.1 (VEGF2) in an Animal Model of Chronic Myocardial Ischemia," *Circulation* 100:I.22 (Dec. 1999).

Vale et al., "Randomized, Single-Blind, Placebo-Controlled Pilot Study of Catheter-Based Myocardial Gene Transfer for Therapeutic Angiogenesis Using Left Ventricular Electromechanical Mapping in Patients with Chronic Myocardial Ischemia," *Circulation* 103:2138-2143 (May 2001).

Walsh et al., "Gene Therapy for Human Hemoglobinopathies," *PSEBM* 204:289-300 (1993).

Williams, R.S. "Southwestern internal medicine conference: prospects for gene therapy of ischemic heart disease," *Am. J. Med. Sci.* 306:129-136 (Aug. 1993).

Yang et al., "Flk-1, a Receptor for Vascular Endothelial Growth Factor (VEGF), Is Expressed by Retinal Progenitor Cells," *J. Neurosci.* 16:6089-6099 (Oct. 1996).

Yourey et al., "Vascular Endothelial Cell Growth Factors Promote the In Vitro Development of Rat Photoreceptor Cells, " *Molecul. Biol. Cell* 10:39a (1999) and 39th Ann. Mtg. Am. Soc. Cell Biol., Washington, DC (1999) (abstract 227).

Yourey et al., "Vascular Endothelial Growth Factors Promote the In Vitro Development of Rat Photoreceptor Cells," *J. Neurosci.* 20:6781-6788 (Sep. 2000).
GenBank Accession No. X68203, Aprelikova et al., "*H.sapiens* mRNA for FLT-4, class III receptor tyrosine kinase," Nov. 30, 1993.
GenBank Accession No. M95200, Claffey et al., "Mouse vascular endothelial growth factor mRNA, complete cds," Apr. 27, 1993.
GenBank Accession No. M24160, Dignam et al., "*C.tentans* 185-kd secretory protein (sp185) mRNA, partial cds, clone pCt185," Apr. 26, 1993.
GenBank Accession No. M24276, Dignam et al., "*C.tentans* 140-kd secretory protein (sp140) mRNA, partial cds, clone pCt140.1," Apr. 26, 1993.
GenBank Accession No. M24277, Dignam et al., "*C.tentans* 140-kd secretory protein (sp140) mRNA, partial cds, clone pCt140.2," Apr. 26, 1993.
GenBank Accession No. D88689, Finnerty et al., "*Mus musculus* mRNA for flt-1, complete cds," Apr. 14, 2000.
GenBank Accession No. L07296, Finnerty et al., "*Mus musculus* receptor tyrosine kinase (FLT4) mRNA, complete cds," Aug. 9, 1993.
GenBank Accession No. X54936, Maglione et al., "*H.sapiens* mRNA for placenta growth factor (PlGF)," Nov. 12, 1991.
GenBank Accession No. S57152, Maglione et al., "*Homo sapiens* placenta growth factor 2 (PlGF-2) gene, partial cds," Mar. 5, 2001.
GenBank Accession No. X59397, Matthews et al., Mouse Flk-1 mRNA for a tyrosine kinase receptor, Nov. 6, 1991.
GenBank Accession No. X52263, Paulsson et al., "*C.tentans* balbiani ring 3 (BR3) gene," Dec. 18, 1992.
GenBank Accession No. M63971, Tischer et al., "Human vascular endothelial cell growth factor gene, exon 1," Aug. 1993.
GenBank Accession No. M63972, Tischer et al., "Human vascular endothelial cell growth factor gene, exon 2," Aug. 3, 1993.
GenBank Accession No. M63973, Tischer et al., "Human vascular endothelial cell growth factor gene, exon 3," Aug. 3, 1993.
GenBank Accession No. M63974, Tischer et al., "Human vascular endothelial cell growth factor gene, exon 4," Aug. 3, 1993.
GenBank Accession No. M63975, Tischer et al., "Human vascular endothelial cell growth factor gene, exon 5," Aug. 3, 1993.
GenBank Accession No. M63976, Tischer et al., "Human vascular endothelial cell growth factor gene, exon 6," Aug. 3, 1993.
GenBank Accession No. M63977, Tischer et al., "Human vascular endothelial cell growth factor gene, exon 7," Aug. 3, 1993.
GenBank Accession No. M63978, Tischer et al., "Human vascular endothelial cell growth factor gene, exon 8," Aug. 3, 1993.
GenBank Accession No. M27281, Keck et al., "Human vascular permeability factor mRNA, complete cds," Aug. 3, 1993.
GenBank Accession No. X04571, Bell et al., "Human mRNA for kidney epidermal growth factor (EGF) precursor," Mar. 21, 1995.
GenBank Accession No. X63556, Corson et al., "*H. sapiens* mRNA for fibrillin," Feb. 17, 1997.
GenBank Accession No. L19896, Corson et al., "Human fibrillin (FBN1) gene, 5' end including alternative exons A, B, and C, and exon M," Nov. 8, 1994.
GenBank Accession No. L04947, Terman et al., "*Homo sapiens* (clones BT3.081.8, BT3.129.5 and BT4.169," Jan. 6, 1995.
GenBank Accession No. M16237, Tanaka et al., "Human c-src-1 proto-oncogene, exon 2," Jan. 13, 1995.
GenBank Accession No. M16243, Tanaka et al., "Human c-src-1 proto-oncogene, exon 3," Jan. 13, 1995.
GenBank Accession No. M16244, Tanaka et al., "Human c-src-1 proto-oncogene, exon 4," Jan. 13, 1995.
GenBank Accession No. M16245, Tanaka et al., "Human c-src-1 proto-oncogene, exon 5," Jan. 13, 1995.
GenBank Accession No. K03212, Anderson et al., "Human c-src-1 proto-oncogene, exon 6," Jan. 13, 1995.
GenBank Accession No. K03213, Anderson et al., "Human c-src-1 proto-oncogene, exon 7," Jan. 13, 1995.
GenBank Accession No. K03214, Anderson et al., "Human c-src-1 proto-oncogene, exon 8," Jan. 13, 1995.
GenBank Accession No. K03215, Anderson et al., "Human c-src-1 proto-oncogene, exon 9," Jan. 13, 1995.
GenBank Accession No. K03216, Tanaka et al., "Human c-src-1 proto-oncogene, exon 10," Jan. 13, 1995.
GenBank Accession No. K03217, Tanaka et al., "Human c-src-1 proto-oncogene, exon 11," Jan. 13, 1995.
GenBank Accession No. K03218, Tanaka et al., "Human c-src-1 proto-oncogene, exon 12," Jan. 13, 1995.
GenBank Accession No. M13994, Tsujimoto et al., "Human B-cell leukemia/lymphoma 2 (bcl-2) proto-oncogene mRNA encoding bcl-2-alpha protein, complete cds" Oct. 31, 1994.
GenBank Accession No. M13995, Tsujimoto et al., "Human B-cell leukemia/lymphoma 2 (bcl-2) proto-oncogene mRNA endocing bcl-3-beta protein, complete cds" Oct. 31, 1994.
GenBank Accession No. L22473, Oltvai et al., "Human Bax alpha mRNA, complete cds," Dec. 15, 1993.
GenBank Accession No. L22474, Oltvai et al., "Human Bax beta mRNA, complete cds," Dec. 13, 1993.
GenBank Accession No. AJ000185, Achen et al., "*Homo sapiens* mRNA for vascular endothelial growth factor-D," Feb. 11, 1998.
GenBank Accession No. S08167, Paulsson et al., "Balbiani ring 3 protein—midge (*Chironomus tentans*)," 1990.
International Search Report, Application No. PCT/US99/05021.
International Search Report, Application No. PCT/US94/05291.
International Search Report, Application No. PCT/US01/24658.
International Search Report, Application No. PCT/US02/26246, mailed May 21, 2003.
Statutory Declaration of Kari Alitalo, executed on Aug. 14, 2002, and accompanying Exhibits KA-1 and KA-2.
Statutory Declaration of Peter Adrian Walton Rogers, executed on Aug. 9, 2002.
Statutory Declaration of Francis John Ballard, executed on Jul. 16, 2002.
Statutory Declaration of Kari Alitalo, executed on Jul. 16, 2002, and accompanying Exhibit 1.
Statutory Declaration of Susan Power, executed on Mar. 22, 2002, and accompanying Appendices I to IV.
Statutory Declaration of Nicholas Kim Hayward, executed on Mar. 26, 2002.
Statutory Declaration of Stuart A. Aaronson, executed on Mar. 22, 2002, and accompanying Appendices I to III.
Statutory Declaration of Gary Baxter Cox, executed on Mar. 22, 2002, and accompanying Exhibit GBC24 (Statutory Declaration of Peter Adrian Walters, executed on Oct. 26, 2001).
Statutory Declaration of Frances John Ballard, executed on Dec. 12, 2001, and accompanying Exhibit 1.
Statutory Declaration of Kari Alitalo, executed on Sep. 24, 2001, and accompanying Exhibit 1 and 2.
Statutory Declaration of Peter Adrian Walton Rogers, executed on Nov. 12, 2001, and accompanying Exhibits PAWR1 to PAWR14.
Statutory Declaration of John Stanley Mattick, executed on Dec. 12, 2000, and accompanying Exhibits JSM1 to JSM4.
Statutory Declaration of Nicholas Kim Hayward, executed on Dec. 8, 2000, and accompanying Exhibits NKH 1 and 2.
Statutory Declaration of Jennifer Ruth Gamble, executed on Dec. 12, 2000, and accompanying Exhibits JRG 1 to 3.
Statutory Declaration of Tom Rapoport, executed on Dec. 13, 2000, and accompanying Exhibits TP 1 and 2.
Statutory Declaration of Stuart A. Aaronson, executed on Dec. 14, 2000, and accompanying CV.
Statutory Declaration of Susan Power, executed on Dec. 13, 2000, and accompanying Appendices 1 to 2 and Figure 1.
Statutory Declaration of Gary Baxter Cox, executed on Dec. 13, 2000, and accompanying Exhibits GBC 1 to 23.
Statutory Declaration of Peter Adrian Walton Rogers, executed on Feb. 16, 2000 and accompanying Exhibit 1.
Statutory Declaration of Frances John Ballard, executed on Feb. 16, 2000, and accompanying Exhibit 1.
Statutory Declaration of Kari Alitalo, executed on Feb. 15, 2000, and accompanying Exhibits 1 to 3.
European Supplementary Search Report, Application No. EP 01963814, mailed Jul. 14, 2004.
Supplementary Partial European Search Report, Application No. EP 02726730, mailed Jan. 10, 2005.
Supplementary Partial European Search Report, Application No. EP 02721715, mailed Jan. 10, 2005.

Supplementary Partial European Search Report, Application No. EP 02721715, mailed Oct. 22, 2004.
EBI Accession No. AAW27553, Knappik et al., "Human Ab heavy chain variable region VH3 consensus," Jan. 23, 1998.
Supplementary European Search Report, Application No. EP 02726730, mailed Oct. 25, 2004.
Supplementary Partial European Search Report, Application No. EP 00905992, mailed Nov. 8, 2004.
Anderson, W.F., "Human gene therapy," *Nature* 392 :25-30, Macmillan Magazines Ltd. (Apr. 1998).
Better et al., "*Escherichia coli* secretion of an active chimeric antibody fragment," *Science* 240:1041-1043, American Association for the Advancement of Science (1988).
Borg, J.-P., et al., "Biochemical characterization of two isoforms of FLT4, a VEGF receptor-related tyrosine kinase," *Oncogene* 10:973-984, Stockton Press (Mar. 1995).
Capogrossi, M.C., "Gene Therapy of Coronary Artery Disease," Project No. Z01 AG00811-01, Abstract (Jan. 1994).
Capogrossi, M.C., "Gene Therapy of Coronary Artery Disease," Project No. Z01 AG00811-02, Abstract (Jan. 1995).
Choi, I.H., et al., "Angiogenesis and Mineralization During Distraction Osteogenesis," *J. Korean Med. Sci.* 17:435-447, The Korean Academy of Medical Sciences (Aug. 2002).
Colwell et al., "Method for generating a high frequency of hybridomas producing monoclonal IgA antibodies," *Methods Enzymol.* 121:42-51, Academic Press (1986).
Danis, R.P., et al., "Anti-angiogenic therapy of proliferative diabetic retinopathy," *Exp. Opin. Pharma.* 2:395-407, Ashley Publications Ltd. (Mar. 2001).
Declaration of Dr. Kari Alitalo, In re. of: U.S. Appl. No. 08/585,895, Alitalo et al., filed Jan. 12, 1996, submitted Nov. 26, 1997.
Dias, S. et al., "Vascular endothelial growth factor (VEGF)-C signaling through FLT-4 (VEGFR-3) mediates leukemic cell proliferation, survival, and resistance to chemotherapy," *Blood* 99:2179-2184, The American Society of Hematology (Mar. 2002).
Enholm, B., et al., "Vascular Endothelial Growth Factor-C: A Growth Factor for Lymphatic and Blood Vascular Endothelial Cells," *Trends Cardiovasc. Med.* 8:292-297, Elsevier Science Inc. (Oct. 1998).
Fan. T.-P.D., et al., "Controlling the vasculature: angiogenesis, anti-angiogenesis and vascular targeting of gene therapy," *Trends Pharmaco. Sci.* 16:57-66, Elsevier Science Ltd. (Feb. 1995).
Ferrara, N., "Vascular Endothelial Growth Factor and the Regulation of angiogenesis," *Recent Prog. Hormone Res.* 55:15-36, The Endocrine Society (Mar. 2000).
Halin, C. and Neri, D., "Antibody-Based Targeting of Angiogenesis," *Crit. Rev. Ther. Drug Carrier Syst.* 18:299-339, Begell House, Inc. (Aug. 2001).
Houck et al., "The vascular endothelial growth factor family: identification of a fourth molecular species and characterization of alternative splicing of RNA," *Mol. Endocrin.* 5:1806-1814, The Endocrine Society (1991).
Isner, J.M., et al., "Arterial Gene Thearpy for Therapeutic Angiogenesis in Patients With Peripheral Artery Disease," *Circulation* 91:2687-2692, American Heart Association, Inc. (Jun. 1995).
Isner, J.M. and Feldman, L.J., "Gene therapy for arterial disease," *Lancet* 344: 1653-1654, The Lancet Ltd. (Dec. 1994).
Isner, J.M., et al., "Physiologic Assessment of Angiogenesis by Arterial Gene Therapy with Vascular Endothelial Growth Factor," *J. Cell. Biochem.* (*Suppl. 21A*):378, Abstract C6-215, Wiley-Liss (Mar./Apr. 1995).
Isner, J.M., "Therapeutic Angiogenesis in Vascular Medicine," Project No. R01 HL53354-01, Abstract (Mar. 1995).
Joosten et al., "The production of antibody fragments and antibody fusion protein by yeasts and filamentous fungi," *Microbiol Cell Fact.* 2:1, BioMed Central (Jan. 2003).
Kubo, H., et al., "Blockade of vascular endothelial growth factor receptor-3 signaling inhibits fibroblast growth factor-2-induced lymphangiogenesis in mouse cornea," *Proc. Natl. Acad. Sci.* 99:8868-8873, The National Academy of Sciences (Jun. 2002).
Kuzuya, M. and Kinsella, J.L., "Induction of Endothelial Cell Differentiation in Vitro by Fibroblast-Derived Solube Factors," *Exp. Cell Res.* 215:310-318, Academic Press, Inc. (Dec. 1994).

Longo, R., et al., "Anti-angiogenic therapy: Rationale, challenges and clinical studies," *Angiogenesis* 5:237-256, Kluwer Academic Publishers (Dec. 2002).
Maher, P.A., "Stimulation of Endothelial Cell Proliferation by Vanadate Is Specific for Microvascular Endothelial Cells," *J. Cell. Physiol.* 151:549-554, Wiley-Liss, Inc. (1992).
Maynard, J. and Georgiou, G., "Antibody Engineering," *Annu. Rev. Biomed. Eng.* 2:339-376, Annual Reviews (Aug. 2000).
Mesri, E.A., et al., "Expression of Vascular Endothelial Growth Factor From a Defective Herpes Simplex Virus Type 1 Amplicon Vector Induces Angiogenesis in Mice," *Circulation Res.* 76:161-167, American Heart Association, Inc. (Feb. 1995).
Morea, V., et al., "Antibody Modeling: Implications for Engineering and Design," *Methods* 20:267-279, Academic Press (Mar. 2000).
Mlhauser, J., et al., "In Vivo Gene Transfer into Porcine Cardiac Cells with a Replication-Deficient Recombinant Adenovirus Vector," *Circulation* 88:I-475, Abstract No. 2558, American Heart Association (Oct. 1993).
Mühlhauser, J., et al., "VEGF$_{165}$ Expressed by a Replication-Deficient Recombinant Adenovirus Vector Induces Angiogenesis In Vivo," *Circulation Res.* 77:1077-1086, American Heart Association, Inc. (Dec. 1995).
Oikawa, T., et al., "Three Isoforms of Platelet-Derived Growth Factors All Have the Capability to Induce Angiogenesis In Vivo," *Biol. Pharm. Bull.* 17:1686-1688, Pharmaceutical Society of Japan (Dec. 1994).
Pajusola, K., et al., "Signalling properties of FLT4, a proteolytically processed receptor tyrosine kinase related to two VEGF receptors," *Oncogene* 9:3545-3555, Macmillan Press Ltd. (Dec. 1994).
Pepper, M.S., et al., "In Vitro Angiogenic and Proteolytic Properties of Bovine Lymphatic Endothelial Cells," *Exp. Cell Res.* 210:298-305, Academic Press, Inc. (Jan. 1994).
Plate, K.H., "From Angiogenesis to lymphantiogenesis," *Nat. Med.* 7:151-152, Nature America, Inc. (Feb. 2001).
Schlaeppi et al., "Characterization of a new potent, in vivo neutralizing monoclonal antibody to human vascular endothelial growth factor," *J Cancer Res. Clin. Oncol.* 125:336-342 (1999).
Skerra et al., "Assembly of a functional immunoglobulin Fv fragment in *Escherichia coli.*" *Science* 240:1038-1041, American Association for the Advancement of Science (1988).
Spranger, J. and Pfeiffer, A.F.H., "New concepts in pathogenesis and treatment of diabetic retinopathy," *Exp. Clin. Endocrinol. Diabetes* 109(*Suppl. 2*):S438-S450, J.A. Barth Verlag (2001).
Symes, J.F. and Sniderman, A.D., "Angiogenesis: potential therapy for ischaemic disease," *Curr. Opin. Lipidol.* 5:305-312, Current Science Ltd. (Aug. 1994).
Takeshita, S., et al., "In Vivo Evidence of Enhanced Angiogenesis Following Direct Arterial Gene Transfer of the Plasmid Encoding Vascular Endothelial Growth Factor," *Circulation* 88:I-476, Abstract No. 2565, American Heart Association (Oct. 1993).
Takeshita, S., et al., "Therapeutic Angiogenesis. A Single Intraarterial Bolus of Vascular Endothelial Growth Factor Augments Revascularization in a Rabbit Ischemic Hind Limb Model," *J. Clin. Invest.* 93:662-670, The American Society of Clinical Investigation, Inc. (Feb. 1994).
Van der Flier, M., et al., "Antibody neutralization of vascular endothelial growth factor (VEGF) fails to attenuate vascular permeability and brain edema in experimental pneumococcal meningitis," *J. Neuroimmunol.* 160:170-177, Elsevier B.V. (Mar. 2005).
Verma et al., "Gene therapy—promises, problems and prospects," *Nature* 389:239-242, Nature Publishing Company (Sep. 1997).
Walsh, D.A., "Angiogenesis and arthritis," *Rheumatology* 38:103-112, British Society for Rheumatology (Feb. 1999).
Walsh, D.A. and Pearson, C.I., "Angiogenesis in the pathogenesis of inflammatory joint and lung diseases," *Arthritis Res.* 3:147-153, BioMed Central Ltd. (Feb. 2001).
Williams, R.S., "Southwestern Internal Medicine Conference: Prospects for Gene Therapy of Ischemic Heart Disease," *Am. J. Med. Sci.* 306:129-136, Lippincott Williams & Wilkins (Aug. 1993).
Winkler, K., et al., "Changing the Antigen Binding Specificity by Single Point Mutations of an Anti-p24 (HIV-1) Antibody," *J. Immunol.* 165:4505-4514, The American Association of Immunologists (Oct. 2000).

Witzenbichler, B., et al., "Vascular Endothelial Growth Factor-C (VEGF-C/VEGF-2) Promotes Angiogenesis in the Setting of Tissue Ischemia," *Am. J. Pathol. 153*:381-394, American Society for Investigative Pathology, Inc. (Aug. 1998).

Yeung, P.K.F., "VEGF-2," *Curr. Opin. Invest. Drugs 2*:796-800, PharmaPress Ltd. (Jun. 2001).

NCBI Entrez, Accession No. AF010302, Mandriota S.J. and Pepper, M.S. (first available Jul. 16, 1997).

Letter from John J. Chicca II, Ph.D., Molecular Diagnostic Services, Inc. regarding a third progress report for a project entitled "Cloning and expression of VEGF-2 gene and the efficacy of VEGF-2 protein utilizing the 3-D collagen angiogenesis assay and proliferation," dated Feb. 16, 2006.

Letter from John J. Chicca II, Ph.D., Molecular Diagnostic Services, Inc. regarding a fourth progress report for a project entitled "Cloning and expression of VEGF-2 gene and the efficacy of VEGF-2 protein utilizing the 3-D collagen angiogenesis assay and proliferation," dated Mar. 14, 2006.

U.S. Appl. No. 11/980,495, inventors Rosen et al., filed Oct. 31, 2007 (Not Published).

U.S. Appl. No. *To be determined*, inventors Rosen et al., filed Apr. 1, 2008 (Not Published).

U.S. Appl. No. 12/258,109, inventors Rosen et al., filed Oct. 24, 2008 (Not Published).

U.S. Appl. No. 12/258,140, inventors Alderson et al., filed Oct. 24, 2008 (Not Published).

Extended European Search Report for European Application No. 08153873.8, dated Oct. 13, 2008, European Patent Office, Berlin, Germany.

Tobe, T., et al., "Evolution of Neovascularization in Mice with Overexpression of Vascular Endotherlial Growth Factor in Photoreceptors," *Invest. Opthalmol. Vis. Sci. 39*:180-188, Association for Research in Vision and Ophthalology (Jan. 1998).

Vinores, S.A., et al., "Cellular mechanisms of blood-retinal barrier dysfunction in macular edema," *Documenta Opthalmologica 97*: 217-228, Kluwer Academic Publishers (Jan. 1999).

```
     GTCCTTCCACCATGCACTCGCTGGGCTTCTTCTCTGTGGCGTGTTCTCTGCTCGCCGCTG
  1  ------+---------+---------+---------+---------+---------+   60
     CAGGAAGGTGGTACGTGAGCGACCCGAAGAAGAGACACCCGCACAAGAGACGAGGCCGAC
              M  H  S  L  G  F  F  S  V  A  C  S  L  L  A  A  A  -

CGCTGCTCCCGGGTCCTCGGGAGGCCCCGCCGCCGCCGCCGCCTTCGAGTCCGGACTCCG
 61  ------+---------+---------+---------+---------+---------+  120
     GCGACGAGGGCCCAGGAGCCCTCCGGGGCGGCGGCGGCGGCGGAAGCTCAGGCCTGAGGC
         L  L  P  G  P  R  E  A  P  A  A  A  A  A  F  E  S  G  L  D  -

ACCTCTCGGACGGGGAGCCCGACGGCGAGGCCACGGCTTATGCAAGCAAAGATCTGG
121  ------+---------+---------+---------+---------+---------+  180
     TGGAGAGCCTGCCCCTCGGGCTGCCGCTCGGGCTGCCGGTGCCGAATACGTTCGTTTCTAGACC
         L  S  D  A  E  P  D  A  G  E  A  T  A  Y  A  S  K  D  L  E  -

AGGAGCAGTTACGGTTCTGTGTCCAGTGTAGATGAACTCATGACTGTACTCTACCAGAAT
181  ------+---------+---------+---------+---------+---------+  240
     TCCTCGTCAATGCCAAGACAGTCACATCTACTTGAGTACTGACATGAGATGGTCTTA
         E  Q  L  R  S  V  S  S  V  D  E  L  M  T  V  L  Y  P  E  Y  -

ATTGGAAAATGTACAAGTGTCAGCTAAGGAAAGGAGGCTGGCAACATAACAGAGAACAGG
241  ------+---------+---------+---------+---------+---------+  300
     TAACCTTTTACATGTTCACAGTCGATTCCTTCCTCCGACCGTTGTATTGTCTCTTGTCC
         W  K  M  Y  K  C  Q  L  R  K  G  G  W  Q  H  N  R  E  Q  A  -

CCAACCCTCAACTCAAGGACAGAAGAGACTATAAAATTGCTGCAGCACATTATAATACAG
```

Fig. 1A

```
301 AGATCTTGAAAAGTATTGATAATGAGTGGAGAAAGACTCAATGCATGCCACGGGAGGTGT
    ----------+---------+---------+---------+---------+---------+ 360
    GGTTGGAGTTGAGTTCCTGTCTTCTGATATTTTAAACGACGTCGTGTAATATTATGTC
      N  L  N  S  R  T  E  E  T  I  K  F  A  A  A  H  Y  N  T  E  -

361 TCTAGAACTTTTCATAACTATTACTCACCTCTTTCTGAGTACTACGGTGCCCCTCCACA
    ----------+---------+---------+---------+---------+---------+ 420
      I  L  K  S  I  D  N  E  W  R  K  T  Q  C  M  P  R  E  V  C  -

421 CATATCTACACCCCTTCCTCAAACCTCAGCGCTGTTTGTGGAAGAAATTTGGAGGTACAC
    ----------+---------+---------+---------+---------+---------+ 480
    GTATAGATGTGGGGAAGGAGTTTGGAGTCGCGACAAACACCTTCTTTAAACCTCCATGTG
      I  D  V  G  K  E  F  G  V  A  T  N  T  F  F  K  P  P  C  V  -

481 ACAGGCAGATGTCTACACCCCCAACGACGTTATCACTCCCGACGTCACGTACTTGTGT
    ----------+---------+---------+---------+---------+---------+ 540
    TGTCCGTCTACAGATGTGGGGTTGCTGCAATAGTGAGGGCTGCAGTGCATGAACACCA
      S  V  Y  R  C  G  G  C  C  N  S  E  G  L  Q  C  M  N  T  S  -

541 CGTGCTCGATGGAGTCGTTCTGCAATAAACTTTAATGTCACGGAGAGAGTTCCGGGGT
    ----------+---------+---------+---------+---------+---------+ 600
    GCACGAGCTACCTCAGCAAGACGTTATTTGAAATTACAGTGCCTCTCTCTCAAGGCCCA
      T  S  Y  L  S  K  T  L  F  E  I  T  V  P  L  S  Q  G  P  K  -

601 AACCAGTAACAATCAGTTTTGCCAATCACACTTCCTGCCGATGCATGTCTAAACTGGATG
    ----------+---------+---------+---------+---------+---------+ 660
    TTGGTCATTGTTAGTCAAAACGGTTAGTGTGAAGGACGGCTACGTACAGATTTGACCTAC
      P  V  T  I  S  F  A  N  H  T  S  C  R  C  M  S  K  L  D  V  -
```

Fig. 1B

```
       TTTACAGACAAGTTCATTCCATTATTAGACGTTCCCTGCCAGCAACACTACCACAGTGTC
661    ------+---------+---------+---------+---------+---------+ 720
       AAATGTCTGTTCAAGTAAGGTAATAATCTGCAAGGACGGTCGTTGTGATGGTGTCACAG
       Y  R  Q  V  H  S  I  I  R  R  S  L  P  A  T  L  P  Q  C  Q  -

AGGCAGCGAACAAGACCTGCCCCACCAATTACATGTGGAATAATCACATCTGCAGATGCC
721    ------+---------+---------+---------+---------+---------+ 780
       TCCGTCGCTTGTTCTGGACGGGGTGGTTAATGTACACCTTATTAGTGTAGACGTCTACGG
       A  A  N  K  T  C  P  T  N  Y  M  W  N  N  H  I  C  R  C  L  -

TGGCTCAGGAAGATTTTATGTTTTCCTCGGATGCTGGAGATGACTCAACAGATGGATTCC
781    ------+---------+---------+---------+---------+---------+ 840
       ACCGAGTCCTTCTAAAATACAAAGGAGCCTACGACCTCTACTGAGTTGTCTACCTAAGG
       A  Q  E  D  F  M  F  S  S  D  A  G  D  D  S  T  D  G  F  H  -

ATGACATCTGTGGACCAAACAAGGAGCTGGATGAAGAGACCTGTCAGTGTGTCTGCAGAG
841    ------+---------+---------+---------+---------+---------+ 900
       TACTGTAGACACCTGGTTTGTTCCTCGACCTACTTCTGGACAGTCACACAGACGTCTC
       D  I  C  G  P  N  K  E  L  D  E  E  T  C  Q  C  V  C  R  A  -

CGGGGCTTCGGCCCTGCCAGTGTGGACCCCCACAAAGAACTAGACAGAAACTCATGCCAGT
901    ------+---------+---------+---------+---------+---------+ 960
       GCCCCGAAGCCGGGACGGTCGACACCTGGGGTGTTTCTTGATCTGTCTTTGAGTACGGTCA
       G  L  R  P  A  S  C  G  P  H  K  E  L  D  R  N  S  C  Q  C  -

GTGTCTGTAAAACAAACTCTTCCCAGCCAATGTGGGCCAACCGAGAATTTGATGAAA
961    ------+---------+---------+---------+---------+---------+ 1020
       CACAGACATTTTGTTTGAGAAGGGTCGGTTACACCCCGGTTGGCTCTTAAACTACTTT
```

Fig.1C

```
        V  C  K  N  K  L  F  P  S  Q  C  G  A  N  R  E  F  D  E  N  -
     ACACATGCCAGTGTGTATGTAAAAAGAACCTGCCCCAGAAATCAACCCCTAAATCCTGGAA
1021 ------------------------------+------------------------------ 1080
     TGTGTACGGTCACACATACATTTTCTTGGACGGGGTCTTTAGTTGGGGATTTAGGACCTT
        T  C  Q  C  V  C  K  R  T  C  P  R  N  Q  P  L  N  P  G  K  -

AATGTGCCTGTGAATGTACAGAAAGTCCACAGAAATGCTTGTTAAAAGGAAAGAAGTTCC
1081 ------------------------------+------------------------------ 1140
     TTACACGGACACTTACATGTCTTTCAGGTGTCTTTACGAACAATTTTCCTTTCTTCAAGG
        C  A  C  E  C  T  E  S  P  Q  K  C  L  L  K  G  K  K  F  H  -

ACCACCAAACATGCAGCTGTTACAGACGGCCATGTACGAACCGCCAGAAGGCTTGTGAGC
1141 ------------------------------+------------------------------ 1200
     TGGTGGTTTGTACGTCGACAATGTCTGCCGGTACATGCTTGGCGGTCTTCCGAACACTCG
        H  Q  T  C  S  C  Y  R  R  P  C  T  N  R  Q  K  A  C  E  P  -

CAGGATTTTCATATAGTGAAGAAGTGTGTCGTTGTCCCTTCATATTGGCAAAGACCAC
1201 ------------------------------+------------------------------ 1260
     GTCCTAAAAGTATATCACTTCTTCACACAGGAAGTATAACCGTTTCTGGTG
        G  F  S  Y  S  E  E  V  C  R  C  V  P  S  Y  W  Q  R  P  Q  -

AAATGAGCTAAGATTGTACTGTTTTTCCAGTTCATCGATTTCTATTATGGAAAACTGTGT
```

Fig. 1D

```
1261 ---------+---------+---------+---------+---------+---------+ 1320
     TTTACTCGATTCTAACATGACAAAAGGTCAAGTAGCTAAAGATAATACCTTTGACACA
                     M  S

1321 ---------+---------+---------+---------+---------+---------+ 1380
     TGCCACAGTAGAACTGTCTCTGTGAACAGAGAGACCCTGTGGGTCCATGCTAACAAGACA

1381 ---------+---------+---------+---------+---------+---------+ 1440
     ACGGTGTCATCTTGACAGACACTTGTCTCTCTGGAACACCCAGGTACGATTGTTTCTGT
     AAGTCTGTCTTTCCTGAACCATGTGGATAACTTTACAGAATTGGACTGGAGCTCATCTG
     TTTCAGACAGAAAGGACTTGGTACACCTATTGAAATGTCTTTACCTGACCTCGAGTAGAC

1441 ---------+---------+---------+---------+---------+---------+ 1500
     CAAAAGGCCTCTTGTAAAGACTGGTTTTCTGCCAATGACCAAACAGCCAAGATTTCCTC
     GTTTCCGGAGAACATTTCTGACCAAAGACGGTTACTGGTTGTCGTTCTAAAGGAG

1501 ---------+---------+---------+---------+---------+---------+ 1560
     TTGTGATTCTTTAAAGAATGACTATATAATTTATTCCACTAAAAATATTGTTTCTGC
     AACACTAAGAAATTTCTTACTGATATATATTAAATAAGGTGATTTTTATAACAAAGACG

1561 ---------+---------+---------+---------+---------+---------+ 1620
     ATTCATTTTTATAGCAACAACAATTGGTAAAACTCACTGTGATCAATATTTTATATCAT
     TAAGTAAAAAATATCGTTGTTGTTAACCATTTGAGTGACACTAGTTATAAAAAAATATAGTA

1621 ---------+---------+---------+---------+----- 1674
     GCAAAATATGTTTAAAATAAAATGAAAATTGTATTTATAAAAAAAAAAAAA
     CGTTTTATACAAATTTTATTTACTTTTAACATAAATATTTTTTTTTTTTT
```

Fig. 1E

```
1                                                                           50
Pdgfa    MRTLACLLL  LGCGYLAHVL  AEEAEIPREV  IERLARSQIH  SIRDLQRLLE
Pdgfb    MNRCWA.LFL  SLCCYLRLVS  AEGDPIPEEL  YEMLSDHSIR  SFDDLQRLLH
Vegf     .....MNFLL  SWHWSLALL   LY........  ..........  .LHHAKWSQA
Vegf2    .....MTV    LYPEYWKMYK  CQ........  ..........  .LRKGGWQHN 51                                                                          100
Pdgfa    IDSVGSEDSL  DTSLRAHGVH  ATKHVPEKRP  LPIRRKRSI.  ......EEAVP
Pdgfb    GDP.GEEDGA  ELDLNMTRSH  SGGELES...  .LARGRRSLG  SLTIAEPAMI
Vegf     APMAE.....  ........GGCQ  NHHEVVKFMD  .VYQR....  ..........
Vegf2    REQANLNSRT  EETIKFAAAH  YNTEILKSID  NEWRK....  ..........

101                                                                         150
Pdgfa    AVCKTRTVIY  EIPRSQVDPT  SANFLIWPPC  VEVKRCTGCC  NTSSVKCQPS
Pdgfb    AECKTRTEVF  EISRRLIDRT  NANFLVWPPC  VEVQRCSGCC  NRNVQCRPT
Vegf     SYCHPIETLV  DIFQEYPDEI  ..EYIFKPSC  VPLMRCGGCC  NDEGLECVPT
Vegf2    TQCMPREVCI  DVGKEFGVAT  ..NTFFKPPC  VSVYRCGGCC  NSEGLQCMNT 151                                                                         200
Pdgfa    RVHHRSVKVA  KVEYVRKKPK  LKEVQVRLEE  HLECAC...  ....AT....
Pdgfb    QVQLRPVQVR  KIEIVRKKPI  FKKATVTLED  HLACKC...  ETVAAARPVT
Vegf     EESNITMQIM  RIK.PH..QG  QHIGEMSFLQ  HNKCECRPKK  DRARQEKKSV
Vegf2    STSYLSKTLF  EIT.VPLSQG  PKPVTISFAN  HTSCRCMSKL  DVYRQVHSII
```

Fig. 2A

```
201
Pdgfa    ....TSLNPD YREEDIDVR.  .......... ..........  ..........  ..........
Pdgfb    RSPGGSQEQR AKTPQTRVTI  RTVRVRRPPK GKHRKFKHTH  DKTALKETLG
Vegf     RGK....... .GKGQKRKRK  KSRYKSWSVY VGARCCLMPW  SLPGPHP...
Vegf2    RRSLPATLPQ CQAANKTCPT  NYMWNNHICR CLAQEDFMFS  SDAGDDSTDG    250

251
Pdgfa    .......... ..........  .......... ..........  ..........
Pdgfb    A......... ..........  .......... ..........  ..........
Vegf     ...CGP.... ..........  ......CSE  RRKHLFVQDP  QTCKCSCKNT
Vegf2    FHDICGPNKE LDEETCQCVC  RAGLRPASCG PHKEL...DR  NSCQCVCKNK    300

301
Pdgfa    .......... ..........  .......... ..........  ..........
Pdgfb    .......... ..........  .......... ..........  ..........
Vegf     .DSRCKARQ  LELNERTCRC  DKPRR..... ..........  ..........
Vegf2    EFDENICQC  VCKRTCPRNQ  PLNPGKCACE CTESPQKCLL                 350

351
Pdgfa    .......... ..........  .......... ..........  ..........
Pdgfb    .......... ..........  .......... ..........  ..........
Vegf     .......... ..........  .......... ..........  ..........
Vegf2    KGKKFHHQTC SCYRRPCTNR  QKACEPGFSY SEEVCRCVPS  YWQRPQMS      398
```

Fig. 2B

Lane 1: 14-C and rainbow M.W. marker
Lane 2: FGF control
Lane 3: VEGF2 (M13-reverse $ forward primers)
Lane 4: VEGF2 (M13-reverse & VEGF-F4 primers)
Lane 5: VEGF2 (M13-reverse & VEGF-F5 primers)

Lane 1: Molelular weight marker
Lane 2: Precipitates containing VEGF2.

SEQUENCE LISTING

```
<160> NUMBER OF SEQ ID NOS: 10

<210> SEQ ID NO 1
<211> LENGTH: 1674
<212> TYPE: DNA
<213> ORGANISM: Homo sapiens
<220> FEATURE:
<221> NAME/KEY: CDS
<222> LOCATION: (12)..(1268)
<220> FEATURE:
<221> NAME/KEY: sig_peptide
<222> LOCATION: (12)..(149)
<220> FEATURE:
<221> NAME/KEY: mat_peptide
<222> LOCATION: (150)..(1268)

<400> SEQUENCE: 1
gtccttccac c atg cac tcg ctg ggc ttc ttc tct gtg gcg tgt tct ctg     50
            Met His Ser Leu Gly Phe Phe Ser Val Ala Cys Ser Leu
```

-continued

```
              -45                 -40                 -35
ctc gcc gct gcg ctg ctc ccg ggt cct cgc gag gcg ccc gcc gcc gcc      98
Leu Ala Ala Ala Leu Leu Pro Gly Pro Arg Glu Ala Pro Ala Ala Ala
              -30                 -25                 -20 gcc gcc ttc gag tcc gga ctc gac ctc tcg gac gcg gag ccc gac gcg     146
Ala Ala Phe Glu Ser Gly Leu Asp Leu Ser Asp Ala Glu Pro Asp Ala
              -15                 -10                 -5 ggc gag gcc acg gct tat gca agc aaa gat ctg gag gag cag tta cgg     194
Gly Glu Ala Thr Ala Tyr Ala Ser Lys Asp Leu Glu Glu Gln Leu Arg
 -1   1                   5                   10                  15 tct gtg tcc agt gta gat gaa ctc atg act gta ctc tac cca gaa tat     242
Ser Val Ser Ser Val Asp Glu Leu Met Thr Val Leu Tyr Pro Glu Tyr
                   20                  25                  30 tgg aaa atg tac aag tgt cag cta agg aaa gga ggc tgg caa cat aac     290
Trp Lys Met Tyr Lys Cys Gln Leu Arg Lys Gly Gly Trp Gln His Asn
                   35                  40                  45 aga gaa cag gcc aac ctc aac tca agg aca gaa gag act ata aaa ttt     338
Arg Glu Gln Ala Asn Leu Asn Ser Arg Thr Glu Glu Thr Ile Lys Phe
              50                  55                  60 gct gca gca cat tat aat aca gag atc ttg aaa agt att gat aat gag     386
Ala Ala Ala His Tyr Asn Thr Glu Ile Leu Lys Ser Ile Asp Asn Glu
              65                  70                  75 tgg aga aag act caa tgc atg cca cgg gag gtg tgt ata gat gtg ggg     434
Trp Arg Lys Thr Gln Cys Met Pro Arg Glu Val Cys Ile Asp Val Gly
 80                  85                  90                  95 aag gag ttt gga gtc gcg aca aac acc ttc ttt aaa cct cca tgt gtg     482
Lys Glu Phe Gly Val Ala Thr Asn Thr Phe Phe Lys Pro Pro Cys Val
                   100                 105                 110 tcc gtc tac aga tgt ggg ggt tgc tgc aat agt gag ggg ctg cag tgc     530
Ser Val Tyr Arg Cys Gly Gly Cys Cys Asn Ser Glu Gly Leu Gln Cys
                   115                 120                 125 atg aac acc agc acg agc tac ctc agc aag acg tta ttt gaa att aca     578
Met Asn Thr Ser Thr Ser Tyr Leu Ser Lys Thr Leu Phe Glu Ile Thr
              130                 135                 140 gtg cct ctc tct caa ggc ccc aaa cca gta aca atc agt ttt gcc aat     626
Val Pro Leu Ser Gln Gly Pro Lys Pro Val Thr Ile Ser Phe Ala Asn
145                 150                 155 cac act tcc tgc cga tgc atg tct aaa ctg gat gtt tac aga caa gtt     674
His Thr Ser Cys Arg Cys Met Ser Lys Leu Asp Val Tyr Arg Gln Val
160                 165                 170                 175 cat tcc att att aga cgt tcc ctg cca gca aca cta cca cag tgt cag     722
His Ser Ile Ile Arg Arg Ser Leu Pro Ala Thr Leu Pro Gln Cys Gln
                   180                 185                 190 gca gcg aac aag acc tgc ccc acc aat tac atg tgg aat aat cac atc     770
Ala Ala Asn Lys Thr Cys Pro Thr Asn Tyr Met Trp Asn Asn His Ile
                   195                 200                 205 tgc aga tgc ctg gct cag gaa gat ttt atg ttt tcc tcg gat gct gga     818
Cys Arg Cys Leu Ala Gln Glu Asp Phe Met Phe Ser Ser Asp Ala Gly
                   210                 215                 220 gat gac tca aca gat gga ttc cat gac atc tgt gga cca aac aag gag     866
Asp Asp Ser Thr Asp Gly Phe His Asp Ile Cys Gly Pro Asn Lys Glu
              225                 230                 235 ctg gat gaa gag acc tgt cag tgt gtc tgc aga gcg ggg ctt cgg cct     914
Leu Asp Glu Glu Thr Cys Gln Cys Val Cys Arg Ala Gly Leu Arg Pro
240                 245                 250                 255 gcc agc tgt gga ccc cac aaa gaa cta gac aga aac tca tgc cag tgt     962
Ala Ser Cys Gly Pro His Lys Glu Leu Asp Arg Asn Ser Cys Gln Cys
                   260                 265                 270 gtc tgt aaa aac aaa ctc ttc ccc agc caa tgt ggg gcc aac cga gaa    1010
```

-continued

```
Val Cys Lys Asn Lys Leu Phe Pro Ser Gln Cys Gly Ala Asn Arg Glu
            275                 280                 285 ttt gat gaa aac aca tgc cag tgt gta tgt aaa aga acc tgc ccc aga      1058
Phe Asp Glu Asn Thr Cys Gln Cys Val Cys Lys Arg Thr Cys Pro Arg
        290                 295                 300 aat caa ccc cta aat cct gga aaa tgt gcc tgt gaa tgt aca gaa agt      1106
Asn Gln Pro Leu Asn Pro Gly Lys Cys Ala Cys Glu Cys Thr Glu Ser
    305                 310                 315 cca cag aaa tgc ttg tta aaa gga aag aag ttc cac cac caa aca tgc      1154
Pro Gln Lys Cys Leu Leu Lys Gly Lys Lys Phe His His Gln Thr Cys
320                 325                 330                 335 agc tgt tac aga cgg cca tgt acg aac cgc cag aag gct tgt gag cca      1202
Ser Cys Tyr Arg Arg Pro Cys Thr Asn Arg Gln Lys Ala Cys Glu Pro
                340                 345                 350 gga ttt tca tat agt gaa gaa gtg tgt cgt tgt gtc cct tca tat tgg      1250
Gly Phe Ser Tyr Ser Glu Glu Val Cys Arg Cys Val Pro Ser Tyr Trp
            355                 360                 365 caa aga cca caa atg agc taagattgta ctgttttcca gttcatcgat             1298
Gln Arg Pro Gln Met Ser
        370 tttctattat ggaaaactgt gttgccacag tagaactgtc tgtgaacaga gagacccttg    1358 tgggtccatg ctaacaaaga caaaagtctg tctttcctga accatgtgga taactttaca   1418 gaaatggact ggagctcatc tgcaaaaggc ctcttgtaaa gactggtttt ctgccaatga   1478 ccaaacagcc aagattttcc tcttgtgatt tctttaaaag aatgactata aatttatttt  1538 ccactaaaaa tattgtttct gcattcattt ttatagcaac aacaattggt aaaactcact   1598 gtgatcaata ttttatatc atgcaaaata tgtttaaaat aaaatgaaaa ttgtatttat    1658 aaaaaaaaaa aaaaaa                                                   1674
```

<210> SEQ ID NO 2
<211> LENGTH: 419
<212> TYPE: PRT
<213> ORGANISM: Homo sapiens

<400> SEQUENCE: 2

```
Met His Ser Leu Gly Phe Phe Ser Val Ala Cys Ser Leu Leu Ala Ala
    -45                 -40                 -35

Ala Leu Leu Pro Gly Pro Arg Glu Ala Pro Ala Ala Ala Ala Ala Phe
-30                 -25                 -20                 -15

Glu Ser Gly Leu Asp Leu Ser Asp Ala Glu Pro Asp Ala Gly Glu Ala
                -10                 -5                  -1  1

Thr Ala Tyr Ala Ser Lys Asp Leu Glu Glu Gln Leu Arg Ser Val Ser
            5                   10                  15

Ser Val Asp Glu Leu Met Thr Val Leu Tyr Pro Glu Tyr Trp Lys Met
        20                  25                  30

Tyr Lys Cys Gln Leu Arg Lys Gly Gly Trp Gln His Asn Arg Glu Gln
    35                  40                  45                  50

Ala Asn Leu Asn Ser Arg Thr Glu Glu Thr Ile Lys Phe Ala Ala Ala
                55                  60                  65

His Tyr Asn Thr Glu Ile Leu Lys Ser Ile Asp Asn Glu Trp Arg Lys
            70                  75                  80

Thr Gln Cys Met Pro Arg Glu Val Cys Ile Asp Val Gly Lys Glu Phe
        85                  90                  95

Gly Val Ala Thr Asn Thr Phe Phe Lys Pro Pro Cys Val Ser Val Tyr
    100                 105                 110
```

```
Arg Cys Gly Gly Cys Cys Asn Ser Glu Gly Leu Gln Cys Met Asn Thr
115                 120                 125                 130

Ser Thr Ser Tyr Leu Ser Lys Thr Leu Phe Glu Ile Thr Val Pro Leu
            135                 140                 145

Ser Gln Gly Pro Lys Pro Val Thr Ile Ser Phe Ala Asn His Thr Ser
        150                 155                 160

Cys Arg Cys Met Ser Lys Leu Asp Val Tyr Arg Gln Val His Ser Ile
    165                 170                 175

Ile Arg Arg Ser Leu Pro Ala Thr Leu Pro Gln Cys Gln Ala Ala Asn
180                 185                 190

Lys Thr Cys Pro Thr Asn Tyr Met Trp Asn Asn His Ile Cys Arg Cys
195                 200                 205                 210

Leu Ala Gln Glu Asp Phe Met Phe Ser Ser Asp Ala Gly Asp Asp Ser
                215                 220                 225

Thr Asp Gly Phe His Asp Ile Cys Gly Pro Asn Lys Glu Leu Asp Glu
            230                 235                 240

Glu Thr Cys Gln Cys Val Cys Arg Ala Gly Leu Arg Pro Ala Ser Cys
    245                 250                 255

Gly Pro His Lys Glu Leu Asp Arg Asn Ser Cys Gln Cys Val Cys Lys
260                 265                 270

Asn Lys Leu Phe Pro Ser Gln Cys Gly Ala Asn Arg Glu Phe Asp Glu
275                 280                 285                 290

Asn Thr Cys Gln Cys Val Cys Lys Arg Thr Cys Pro Arg Asn Gln Pro
            295                 300                 305

Leu Asn Pro Gly Lys Cys Ala Cys Glu Cys Thr Glu Ser Pro Gln Lys
            310                 315                 320

Cys Leu Leu Lys Gly Lys Lys Phe His His Gln Thr Cys Ser Cys Tyr
        325                 330                 335

Arg Arg Pro Cys Thr Asn Arg Gln Lys Ala Cys Glu Pro Gly Phe Ser
    340                 345                 350

Tyr Ser Glu Glu Val Cys Arg Cys Val Pro Ser Tyr Trp Gln Arg Pro
355                 360                 365                 370

Gln Met Ser

<210> SEQ ID NO 3
<211> LENGTH: 196
<212> TYPE: PRT
<213> ORGANISM: Homo sapiens

<400> SEQUENCE: 3

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110
```

```
Thr Ser Ala Asn Phe Leu Ile Trp Pro Pro Cys Val Glu Val Lys Arg
        115                 120                 125

Cys Thr Gly Cys Cys Asn Thr Ser Val Lys Cys Gln Pro Ser Arg
        130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
                180                 185                 190

Thr Asp Val Arg
        195

<210> SEQ ID NO 4
<211> LENGTH: 241
<212> TYPE: PRT
<213> ORGANISM: Homo sapiens

<400> SEQUENCE: 4

Met Asn Arg Cys Trp Ala Leu Phe Leu Ser Leu Cys Cys Tyr Leu Arg
  1               5                  10                  15

Leu Val Ser Ala Glu Gly Asp Pro Ile Pro Glu Glu Leu Tyr Glu Met
                20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
        50                  55                  60

Thr Arg Ser His Ser Gly Gly Glu Leu Glu Ser Leu Ala Arg Gly Arg
 65                 70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 5
<211> LENGTH: 232
<212> TYPE: PRT
<213> ORGANISM: Homo sapiens
```

```
<400> SEQUENCE: 5

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Lys Asn Glu Arg Thr
    210                 215                 220

Cys Arg Cys Asp Lys Pro Arg Arg
225                 230

<210> SEQ ID NO 6
<211> LENGTH: 14
<212> TYPE: PRT
<213> ORGANISM: Homo sapiens

<400> SEQUENCE: 6

Pro Xaa Cys Val Xaa Xaa Xaa Arg Cys Xaa Gly Cys Cys Asn
 1               5                  10

<210> SEQ ID NO 7
<211> LENGTH: 50
<212> TYPE: DNA
<213> ORGANISM: Homo sapiens

<400> SEQUENCE: 7
tgtaatacga ctcactatag ggatcccgcc atggaggcca cggcttatgc          50

<210> SEQ ID NO 8
<211> LENGTH: 28
<212> TYPE: DNA
<213> ORGANISM: Homo sapiens

<400> SEQUENCE: 8
gatctctaga ttagctcatt tgtggtct                                  28
```

-continued

```
<210> SEQ ID NO 9
<211> LENGTH: 27
<212> TYPE: DNA
<213> ORGANISM: Homo sapiens

<400> SEQUENCE: 9
cgcggatcca tgactgtact ctaccca                                          27

<210> SEQ ID NO 10
<211> LENGTH: 60
<212> TYPE: DNA
<213> ORGANISM: Homo sapiens

<400> SEQUENCE: 10
cgctctagat caagcgtagt ctgggacgtc gtatgggtac tcgaggctca tttgtggtct      60
```

ANTIBODIES TO HUMAN VASCULAR ENDOTHELIAL GROWTH FACTOR 2 AND METHODS OF USING THE SAME

This application is a continuation of U.S. application Ser. No. 10/023,584, filed Dec. 21, 2001, which issued as U.S. Pat. No. 7,109,308 on Sep. 19, 2006; which is a divisional of U.S. application Ser. No. 08/465,968, filed Jun. 6, 1995, which issued as U.S. Pat. No. 6,608,182 on Aug. 19, 2003; which is a continuation-in-part of U.S. application Ser. No. 08/207,550, filed Mar. 8, 1994, now abandoned.

This invention relates to newly identified polynucleotides, polypeptides encoded by such polynucleotides, the use of such polynucleotides and polypeptides, as well as the production of such polynucleotides and polypeptides. The polypeptide of the present invention has been identified as a member of the vascular endothelial growth factor family. More particularly, the polypeptide of the present invention is vascular endothelial growth factor 2, sometimes hereinafter referred to as "VEGF2." The invention also relates to inhibiting the action of such polypeptide.

The formation of new blood vessels, or angiogenesis, is essential for embryonic development, subsequent growth, and tissue repair. Angiogenesis, however, is an essential part of certain pathological conditions such as neoplasia, for example, tumors and gliomas, and abnormal angiogenesis is associated with other diseases such as inflammation, rheumatoid arthritis, psoriasis, and diabetic retinopathy (Folkman, J. and Klagsbrun, M., Science 235:442-447, (1987)).

Both acidic and basic fibroblast growth factor molecules are mitogens for endothelial cells and other cell types. Angiotropin and angiogenin can induce angiogenesis, although their functions are unclear (Folkman, J., 1993, Cancer Medicine pp. 153-170, Lea and Febiger Press). A highly selective mitogen for vascular endothelial cells is vascular endothelial growth factor or VEGF (Ferrara, N., et al., Endocr. Rev. 13:19-32, (1992)), also known as vascular permeability factor (VPF). Vascular endothelial growth factor is a secreted angiogenic mitogen whose target cell specificity appears to be restricted to vascular endothelial cells.

The murine VEGF gene has been characterized and its expression pattern in embryogenesis has been analyzed. A persistent expression of VEGF was observed in epithelial cells adjacent to fenestrated endothelium, e.g., in choroid plexus and kidney glomeruli. The data was consistent with a role of VEGF as a multifuinctional regulator of endothelial cell growth and differentiation (Breier, G. et al. Development, 114:521-532 (1992)).

VEGF is structurally related to the α and β chains of platelet-derived growth factor (PDGF), a mitogen for mesenchymal cells and placenta growth factor (PLGF), an endothelial cell mitogen. These three proteins belong to the same family and share a conserved motif. Eight cysteine residues contributing to disulfide-bond formation are strictly conserved in these proteins. Alternatively spliced mRNAs have been identified for both VEGF, PLGF and PDGF and these different splicing products differ in biological activity and in receptor-binding specificity. VEGF and PDGF function as homo-dimers or hetero-dimers and bind to receptors which elicit intrinsic tyrosine kinase activity following receptor dimerization.

VEGF has four different forms of 121, 165, 189 and 206 amino acids due to alternative splicing. VEGF121 and VEGF165 are soluble and are capable of promoting angiogenesis, whereas VEGF189 and VEGF206 are bound to heparin containing proteoglycans in the cell surface. The temporal and spatial expression of VEGF has been correlated with physiological proliferation of the blood vessels (Gajdusek, C. M., and Carbon, S. J., Cell Physiol., 139:570-579, (1989)); McNeil, P. L., Muthukrishnan, L., Warder, E., D'Amore, P. A., J. Cell. Biol., 109:811-822, (1989)). Its high affinity binding sites are localized only on endothelial cells in tissue sections (Jakeman, L. B., et al., Clin. Invest. 89:244-253, (1989)). The factor can be isolated from pituitary cells and several tumor cell lines, and has been implicated in some human gliomas (Plate, K. H. Nature 359:845-848, (1992)). Interestingly, expression of VEGF121 or VEGF165 confers on Chinese hamster ovary cells the ability to form tumors in nude mice (Ferrara, N., et al., J. Clin. Invest. 91:160-170, (1993)). The inhibition of VEGF function by anti-VEGF monoclonal antibodies was shown to inhibit tumor growth in immune-deficient mice (Kim, K. J., Nature 362:841-844, (1993)). Further, a dominant-negative mutant of the VEGF receptor has been shown to inhibit growth of glioblastomas in mice.

Vascular permeability factor, has also been found to be responsible for persistent microvascular hyperpermeability to plasma proteins even after the cessation of injury, which is a characteristic feature of normal wound healing. This suggests that VPF is an important factor in wound healing. Brown, L. F. et al., J. Exp. Med., 176:1375-9 (1992).

The expression of VEGF is high in vascularized tissues, (e.g., lung, heart, placenta and solid tumors) and correlates with angiogenesis both temporally and spatially. VEGF has also been shown to induce angiogenesis in vivo. Since angiogenesis is essential for the repair of normal tissues, especially vascular tissues, VEGF has been proposed for use in promoting vascular tissue repair (e.g., in atherosclerosis).

U.S. Pat. No. 5,073,492, issued Dec. 17, 1991 to Chen et al., discloses a method for synergistically enhancing endothelial cell growth in an appropriate environment which comprises adding to the environment, VEGF, effectors and serum-derived factor. Also, vascular endothelial cell growth factor C sub-unit DNA has been prepared by polymerase chain reaction techniques. The DNA encodes a protein that may exist as either a hetero-dimer or homo-dimer. The protein is a mammalian vascular endothelial cell mitogen and, as such, is useful for the promotion of vascular development and repair, as disclosed in European Patent Application No. 92302750.2, published Sep. 30, 1992.

The polypeptides of the present invention have been putatively identified as a novel vascular endothelial growth factor based on amino acid sequence homology to human VEGF.

In accordance with one aspect of the present invention, there are provided novel mature polypeptides, as well as biologically active and diagnostically or therapeutically useful fragments, analogs and derivatives thereof. The polypeptides of the present invention are of human origin.

In accordance with another aspect of the present invention, there are provided isolated nucleic acid molecules encoding the polypeptides of the present invention, including mRNAs, DNAs, cDNAs, genomic DNA as well as biologically active and diagnostically or therapeutically useful fragments, analogs and derivatives thereof.

In accordance with still another aspect of the present invention, there are provided processes for producing such polypeptides by recombinant techniques comprising culturing recombinant prokaryotic and/or eukaryotic host cells, containing a nucleic acid sequence encoding a polypeptide of the present invention, under conditions promoting expression of said proteins and subsequent recovery of said proteins.

In accordance with yet a further aspect of the present invention, there is provided a process for utilizing such polypeptide, or polynucleotide encoding such polypeptide for therapeutic purposes, for example, to stimulate angiogenesis, wound-healing, and to promote vascular tissue repair.

In accordance with yet another aspect of the present invention, there are provided antibodies against such polypeptides.

In accordance with yet another aspect of the present invention, there are provided antagonists to such polypeptides, which may be used to inhibit the action of such polypeptides, for example, to inhibit the growth of tumors, to treat diabetic retinopathy, inflammation, rheumatoid arthritis and psoriasis.

In accordance with another aspect of the present invention, there are provided nucleic acid probes comprising nucleic acid molecules of sufficient length to specifically hybridize to nucleic acid sequences of the present invention.

In accordance with another aspect of the present invention, there are provided methods of diagnosing diseases or a susceptibility to diseases related to mutations in nucleic acid sequences of the present invention and proteins encoded by such nucleic acid sequences.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE DRAWINGS

FIGS. 1A-E shows the cDNA sequence (SEQ ID NO:1) and the corresponding deduced amino acid sequence (SEQ ID NO:2) of the polypeptide of the present invention. The standard one letter abbreviations for amino acids are used. Sequencing was performed using 373 Automated DNA Sequencer (Applied Biosystems, Inc.). Sequencing accuracy is predicted to be greater than 97%.

FIGS. 2A-B is an illustration of the amino acid sequence homology between the polypeptide of the present invention and other members of the human PDGF/VEGF family. The boxed areas indicate the conserved sequences and the location of the eight conserved cysteine residues. The amino acid sequences shown in FIGS. 2A-B at comparative lines 1-3 (SEQ ID NOs:3-5, respectively) and the fourth line (corresponding to amino acids 24 to 373 in SEQ ID NO:2) are represented by the conventional one-letter amino acid codes.

Figure 3:
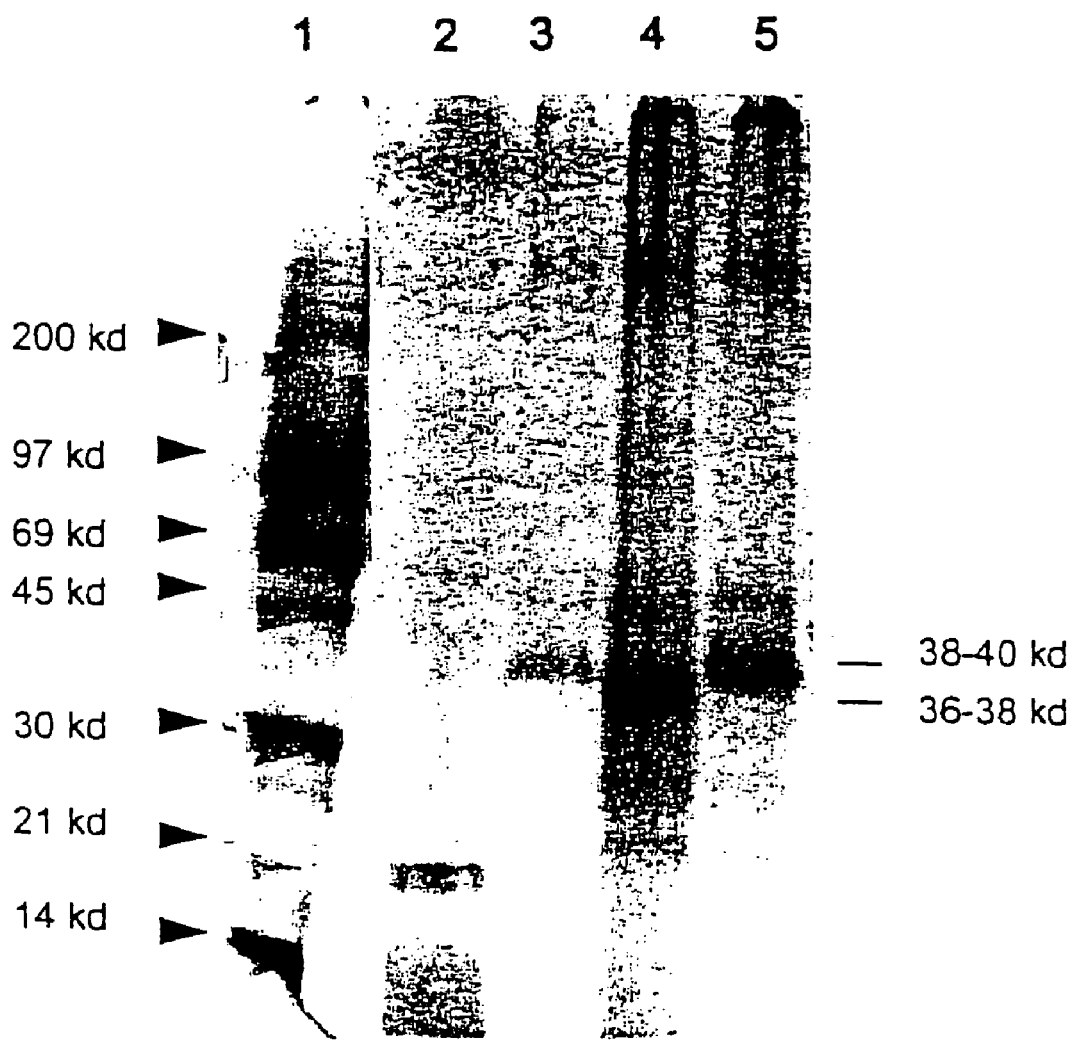
FIG. 3 shows a photograph of a gel after in vitro transcription, translation and electrophoresis of the polypeptide of the present invention. Lane 1: $^{14}C$ and rainbow M.W. marker; Lane 2: FGF control; Lane 3: VEGF2 produced by M13-reverse and forward primers; Lane 4: VEGF2 produced by M13 reverse and VEGF-F4 primers; Lane 5: VEGF2 produced by M13 reverse and VEGF-F5 primers.

The term "gene" means the segment of DNA involved in producing a polypeptide chain; it includes regions preceding and following the coding region (leader and trailer), as well as intervening sequences (introns) between individual coding segments (exons).

In accordance with one aspect of the present invention, there are provided isolated nucleic acid molecules (polynucleotides) which encode for the mature polypeptides having the deduced amino acid sequence of FIGS. 1A-E or for the mature polypeptide encoded by the cDNA of the clone deposited as ATCC Deposit No. 97149 on May 12, 1995 or for polypeptides which have fewer amino acid residues than those showing in FIGS. 1A-E. This deposit is a biological deposit made with the ATCC, 10801 University Boulevard, Manassas, Va. 20110-2209 on the above date.

A polynucleotide encoding a polypeptide of the present invention may be obtained from early stage human embryo (week 8 to 9) osteoclastomas, adult heart or several breast cancer cell lines. The polynucleotide of this invention was discovered in a cDNA library derived from early stage human embryo week 9. It is structurally related to the VEGF/PDGF family. VEGF2 contains an open reading frame encoding a protein of 419 amino acid residues of which approximately the first 23 amino acid residues are the putative leader sequence such that the mature protein comprises 396 amino acids, and which protein exhibits the highest amino acid sequence homology to human vascular endothelial growth factor (30% identity), followed by PDGFα (23%) and PDGFβ (22%).

It is particularly important that all eight cysteines are conserved within all four members of the family (see boxed areas of FIGS. 2A-B). In addition, the signature for the PDGF/VEGF family, PXCVXXXRCXGCCN (SEQ ID NO:6), is conserved in VEGF2 (see FIGS. 2A-B).

The VEGF2 polypeptide of the present invention is meant to include the full length polypeptide and polynucleotide sequence which encodes for any leader sequences and for active fragments of the full length polypeptide. Active fragments are meant to include any portions of the full length amino acid sequence which have less than the full 419 amino acids of the full length amino acid sequence as shown in SEQ ID No. 2 and FIGS. 2A-B, but still contain the eight cysteine residues shown conserved in FIGS. 2A-B and such fragments still contain VEGF2 activity.

There are at least two alternatively spliced VEGF2 mRNA sequences present in normal tissues. The size of the two VEGF2 mRNA sequences which correspond to the full-length and truncated version respectively are shown in FIG. 3, lane 5 shows two bands indicating the presence of the alternatively spliced mRNA encoding the VEGF2 polypeptide of the present invention.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A-E or that of the deposited clone or may be a different coding sequence which coding sequence, as a result of the redundancy or degeneracy of the genetic code, encodes the same mature polypeptide as the DNA of FIGS. 1A-E or the deposited cDNA.

The polynucleotide which encodes for the mature polypeptide of FIGS. 1A-E or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A-E or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A-E or the same mature polypeptide encoded by the cDNA of the deposited clone as well as variants of such polynucleotides which variants encode for a fragment, derivative or analog of the polypeptide of FIGS. 1A-E or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A-E or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A-E (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptides which have the deduced amino acid sequence of FIGS. 1A-E or which has the amino acid sequence encoded by the deposited cDNA, as well as fragments, analogs and derivatives of such polypeptide.

The terms "fragment," "derivative" and "analog" when referring to the polypeptide of FIGS. 1A-E or that encoded by the deposited cDNA, means a polypeptide which retains the conserved motif of VEGF proteins as shown in FIGS. 2A-B and essentially the same biological function or activity.

The polypeptides of the present invention may be recombinant polypeptides, natural polypeptides or synthetic polypeptides, preferably recombinant polypeptides.

The fragment, derivative or analog of the polypeptide of FIGS. 1A-E or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide or (v) one in which comprises fewer amino acid residues shown in SEQ ID No. 2 and retains the conserved motif and yet still retains activity characteristic of the VEGF family of polypeptides. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 95% identity) to the polypeptide of SEQ ID NO:2 and still more preferably at least 95% similarity (still more preferably at least 90% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the VEGF2 genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium;* fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); ptrc99a, pKK223-3, pKK233-3, pDR540, pRIT5 (Pharmacia). Eukaryotic: pWL-NEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Figure 8:
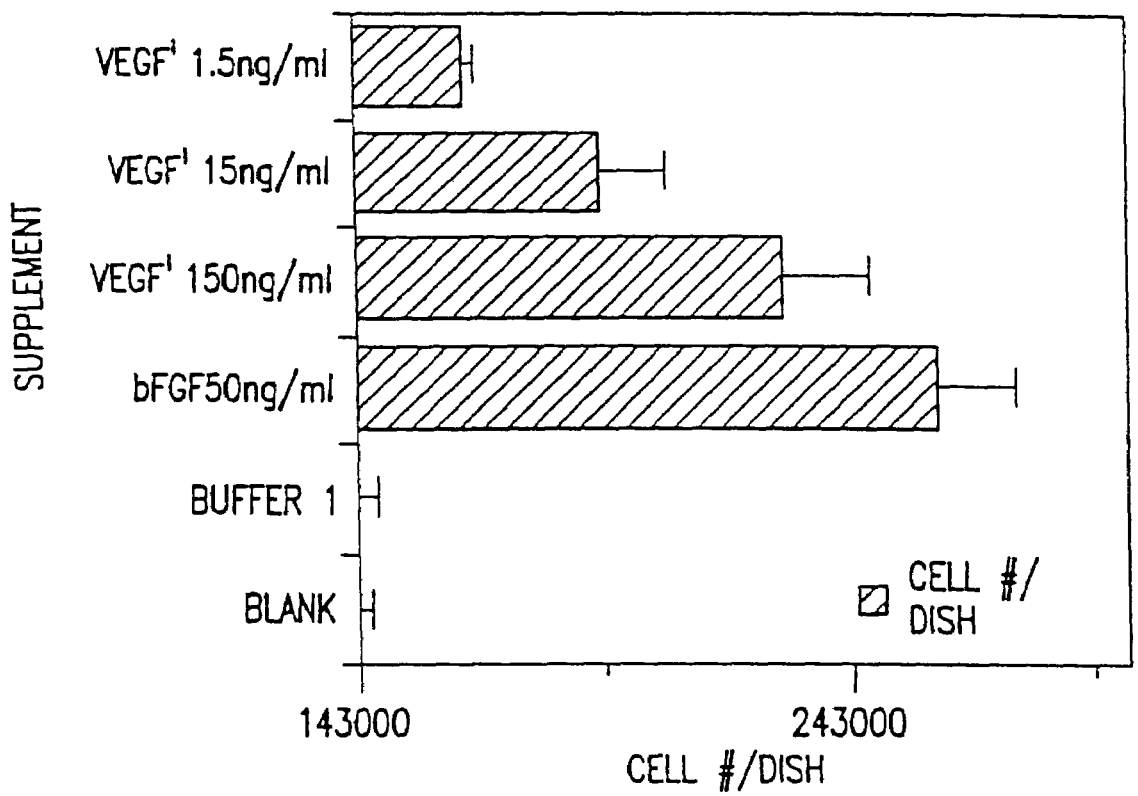
FIG. 8 illustrates the effect of partially-purified VEGF2 protein on the growth of vascular endothelial cells in comparison to basic fibroblast growth factor.
Figure 9:
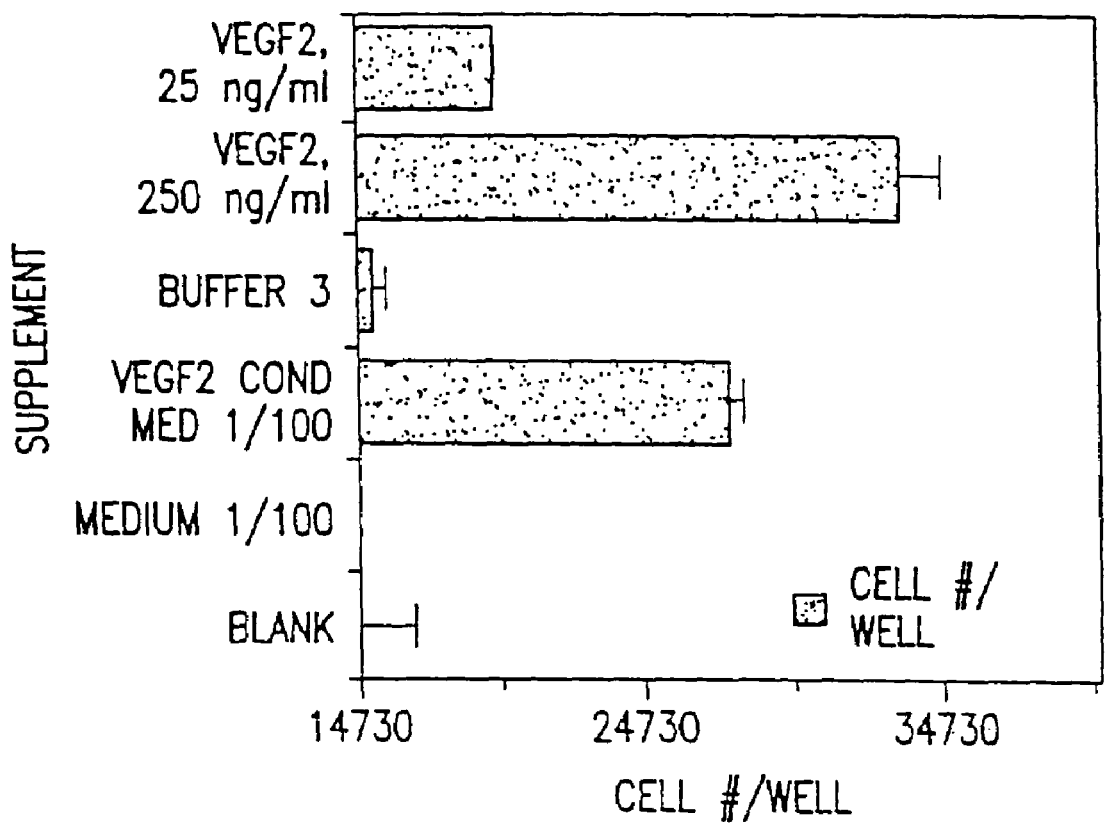
FIG. 9 illustrates the effect of purified VEGF2 protein on the growth of vascular endothelial cells.

As shown in FIGS. 8 and 9, the VEGF2 polypeptide of SEQ ID No. 2, minus the initial 46 amino acids, is a potent mitogen for vascular endothelial cells and stimulates their growth and proliferation. The results of a Northern blot analysis performed for the VEGF2 nucleic acid sequence encoding this polypeptide wherein 20 μg of RNA from several human tissues were probed with $^{32}$P-VEGF2, illustrates that this protein is actively expressed in the heart and lung which is further evidence of mitogenic activity.

Accordingly, VEGF2 may be employed to promote angiogenesis, for example, to stimulate the growth of transplanted tissue where coronary bypass surgery is performed. VEGF2 may also be employed to promote wound healing, particularly to re-vascularize damaged tissues or stimulate collateral blood flow during ischemia and where new capillary angiogenesis is desired. VEGF2 may be employed to treat full-thickness wounds such as dermal ulcers, including pressure sores, venous ulcers, and diabetic ulcers. In addition, VEGF2 may be employed to treat full-thickness burns and injuries where a skin graft or flap is used to repair such burns and injuries. VEGF2 may also be employed for use in plastic surgery, for example, for the repair of lacerations from trauma and cuts in association with surgery.

Along these same lines, VEGF2 may be employed to induce the growth of damaged bone, periodontium or ligament tissue. VEGF2 may also be employed for regenerating supporting tissues of the teeth, including cementum and periodontal ligament, that have been damaged by disease and trauma.

Since angiogenesis is important in keeping wounds clean and non-infected, VEGF2 may be employed in association with surgery and following the repair of cuts. It may also be employed for the treatment of abdominal wounds where there is a high risk of infection.

VEGF2 may be employed for the promotion of endothelialization in vascular graft surgery. In the case of vascular grafts using either transplanted or synthetic material, VEGF2 can be applied to the surface of the graft or at the junction to promote the growth of vascular endothelial cells. VEGF2 may also be employed to repair damage of myocardial tissue as a result of myocardial infarction. VEGF2 may also be employed to repair the cardiac vascular system after ischemia. VEGF2 may also be employed to treat damaged vascular tissue as a result of coronary artery disease and peripheral and CNS vascular disease.

VEGF2 may also be employed to coat artificial prostheses or natural organs which are to be transplanted in the body to minimize rejection of the transplanted material and to stimulate vascularization of the transplanted materials.

VEGF2 may also be employed for vascular tissue repair, for example, that occurring during arteriosclerosis and required following balloon angioplasty where vascular tissues are damaged.

VEGF2 nucleic acid sequences and VEGF2 polypeptides may also be employed for in vitro purposes related to scientific research, synthesis of DNA and manufacture of DNA vectors, and for the production of diagnostics and therapeutics to treat human disease. For example, VEGF2 may be employed for in vitro culturing of vascular endothelial cells, where it is added to the conditional medium in a concentration from 10 pg/ml to 10 ng/ml.

Fragments of the full length VEGF2 gene may be used as a hybridization probe for a cDNA library to isolate other genes which have a high sequence similarity to the gene or similar biological activity. Probes of this type generally have at least 50 base pairs, although they may have a greater number of bases. The probe may also be used to identify a cDNA clone corresponding to a full length transcript and a genomic clone or clones that contain the complete VEGF2 gene including regulatory and promotor regions, exons, and introns. An example of a screen comprises isolating the coding region of the VEGF2 gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides methods for identification of VEGF2 receptors. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to VEGF2, and a cDNA library created from this RNA is divided into pools and used to transfect COS cells or other cells that are not responsive to VEGF2. Transfected cells which are grown on glass slides are exposed to labeled VEGF2. VEGF2 can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled VEGF2 can be photoaffinity linked with cell membrane or extract preparations that express the receptor molecule. Cross-linked material is resolved by PAGE and exposed to X-ray film. The labeled complex containing VEGF2 is then excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention is also related to a method of screening compounds to identify those which are VEGF2 agonists or antagonists. An example of such a method takes advantage of the ability of VEGF2 to significantly stimulate the proliferation of human endothelial cells in the presence of the comitogen Con A. Endothelial cells are obtained and cultured in 96-well flat-bottomed culture plates (Costar, Cambridge, Mass.) in a reaction mixture supplemented with Con-A (Calbiochem, La Jolla, Calif.). Con-A, polypeptides of the present invention and the compound to be screened are added. After incubation at 37 C, cultures are pulsed with 1 μCi of $^3$[H] thymidine (5 Ci/mmol; 1 Ci=37 BGq; NEN) for a sufficient time to incorporate the $^3$[H] and harvested onto glass fiber filters (Cambridge Technology, Watertown, Mass.). Mean $^3$[H]-thymidine incorporation (cpm) of triplicate cultures is determined using a liquid scintillation counter (Beckman Instruments, Irvine, Calif.). Significant $^3$[H]thymidine incorporation, as compared to a control assay where the compound is excluded, indicates stimulation of endothelial cell proliferation.

To assay for antagonists, the assay described above is performed and the ability of the compound to inhibit $^3$[H]thymidine incorporation in the presence of VEGF2 indicates that the compound is an antagonist to VEGF2. Alternatively, VEGF2 antagonists may be detected by combining VEGF2 and a potential antagonist with membrane-bound VEGF2 receptors or recombinant receptors under appropriate conditions for a competitive inhibition assay. VEGF2 can be labeled, such as by radioactivity, such that the number of VEGF2 molecules bound to the receptor can determine the effectiveness of the potential antagonist.

Alternatively, the response of a known second messenger system following interaction of VEGF2 and receptor would be measured and compared in the presence or absence of the compound. Such second messenger systems include but are not limited to, cAMP guanylate cyclase, ion channels or phosphoinositide hydrolysis. In another method, a mammalian cell or membrane preparation expressing the VEGF2 receptor is incubated with labeled VEGF2 in the presence of the compound. The ability of the compound to enhance or block this interaction could then be measured.

Potential VEGF2 antagonists include an antibody, or in some cases, an oligonucleotide, which bind to the polypeptide and effectively eliminate VEGF2 function. Alternatively, a potential antagonist may be a closely related protein which binds to VEGF2 receptors, however, they are inactive forms of the polypeptide and thereby prevent the action of VEGF2. Examples of these antagonists include a negative dominant mutant of the VEGF2 polypeptide, for example, one chain of the hetero-dimeric form of VEGF2 may be dominant and may be mutated such that biological activity is not retained. An example of a negative dominant mutant includes truncated versions of a dimeric VEGF2 which is capable of interacting with another dimer to form wild type VEGF2, however, the resulting homo-dimer is inactive and fails to exhibit characteristic VEGF activity.

Another potential VEGF2 antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of VEGF2. The antisense RNA oligonucleotide hybridizes to the mRNA in vivo and blocks translation of the mRNA molecule into the VEGF2 polypeptide (Antisense— Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of VEGF2.

Potential VEGF2 antagonists also include small molecules which bind to and occupy the active site of the polypeptide thereby making the catalytic site inaccessible to substrate such that normal biological activity is prevented. Examples of small molecules include but are not limited to small peptides or peptide-like molecules.

The antagonists may be employed to limit angiogenesis necessary for solid tumor metastasis.

The mRNA encoding for VEGF2 is found to be expressed at moderate levels in at least two breast tumor cell lines which is indicative of the role of VEGF2 polypeptides in the malignant phenotype. Gliomas are also a type of neoplasia which may be treated with the antagonists of the present invention.

The antagonists may also be used to treat chronic inflammation caused by increased vascular permeability. In addition to these disorders, the antagonists may also be employed to treat retinopathy associated with diabetes, rheumatoid arthritis and psoriasis.

The antagonists may be employed in a composition with a pharmaceutically acceptable carrier, e.g., as hereinafter described.

The VEGF2 polypeptides and agonists and antagonists may be employed in combination with a suitable pharmaceutical carrier. Such compositions comprise a therapeutically effective amount of the polypeptide or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the pharmaceutical compositions are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The VEGF2 polypeptides, and agonists or antagonists which are polypeptides may also be employed in accordance with the present invention by expression of such polypeptide in vivo, which is often referred to as "gene therapy."

Thus, for example, cells such as bone marrow cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding the polypeptide of the present invention.

Similarly, cells may be engineered in vivo for expression of a polypeptide in vivo, for example, by procedures known in the art. As known in the art, a producer cell for producing a retroviral particle containing RNA encoding a polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the VEGF2 gene as part of a diagnostic assay for detecting diseases or susceptibility to diseases related to the presence of mutations in VEGF2 nucleic acid sequences.

Individuals carrying mutations in the VEGF2 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163-166 (1986)) prior to analysis. RNA or cDNA may also be used for the same purpose. As an example, PCR primers complementary to the nucleic acid encoding VEGF2 can be used to identify and analyze VEGF2 mutations. For example, deletions and insertions can be detected by a change in size of the amplified product in comparison to the normal genotype. Point mutations can be identified by hybridizing amplified DNA to radiolabeled VEGF2 RNA or alternatively, radiolabeled VEGF2 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397-4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of VEGF2 protein in various tissues since an over-expression of the proteins compared to normal control tissue samples may detect the presence of a disease or susceptibility to a disease, for example, abnormal cellular differentiation. Assays used to detect levels of VEGF2 protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the VEGF2 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein, such as, bovine serum albumen. Next, the monoclonal antibody is incubated in the dish during which time the monoclonal antibodies attach to any VEGF2 proteins attached to the polystyrene dish. All unbound monoclonal antibody is washed out with buffer. The reporter antibody linked to horseradish peroxidase is placed in the dish resulting in binding of the reporter antibody to any monoclonal antibody bound to VEGF2. Unattached reporter antibody is then washed out. Peroxidase substrates are then added to the dish and the amount of color developed in a given time period is a measurement of the amount of VEGF2 protein present in a given volume of patient sample when compared against a standard curve.

A competition assay may be employed wherein antibodies specific to VEGF2 are attached to a solid support. Polypeptides of the present invention are then labeled, for example, by radioactivity, and a sample derived from the host are passed over the solid support and the amount of label detected, for example by liquid scintillation chromatography, can be correlated to a quantity of VEGF2 in the sample.

A "sandwich" assay is similar to an ELISA assay. In a "sandwich" assay VEGF2 is passed over a solid support and binds to antibody attached to a solid support. A second antibody is then bound to the VEGF2. A third antibody which is labeled and specific to the second antibody is then passed over the solid support and binds to the second antibody and an amount can then be quantified.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques. Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide. For preparation of monoclonal antibodies, any technique which provides antibodies produced by continuous cell line cultures can be used. Examples include the hybridoma technique (Kohler and Milstein, 1975, Nature, 256: 495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described by the method of Graham, F. and Van der Eb, A., Virology, 52:456-457 (1973).

EXAMPLE 1

Expression Pattern of VEGF2 in Human Tissues and Breast Cancer Cell Lines

Northern blot analysis was carried out to examine the levels of expression of the VEGF2 gene in human tissues and human breast cancer cell lines. Total cellular RNA samples were isolated with RNAzol™ B system (Biotecx Laboratories, Inc.). About 10 µg of total RNA isolated from each breast tissue and cell line specified was separated on 1% agarose gel and blotted onto a nylon filter, (Molecular Cloning, Sambrook Fritsch, and Maniatis, Cold Spring Harbor Press, 1989). The labeling reaction was done according to the Stratagene Cloning Systems, Inc., Prime-It kit with 50 ng DNA fragment. The labeled DNA was purified with a Select-G-50 column from 5 Prime-3 Prime, Inc, Boulder, Colo., USA. The filter was then hybridized with radioactively labeled full length VEGF2 gene at 1,000,000 cpm/ml in 0.5 M $NaPO_4$ and 7% SDS overnight at 65° C. After washing twice at room temperature and twice at 60° C. with 0.5×SSC, 0.1% SDS, the filters were then exposed at –70° C. overnight with an intensifying screen. A message of 1.6 Kb was observed in 2 breast cancer cell lines.

EXAMPLE 2

Cloning and Expression of VEGF2 Using the Baculovirus Expression System

The DNA sequence encoding the VEGF2 protein without 46 amino acids at the N-terminus, ATCC No. 97149, was amplified using PCR oligonucleotide primers corresponding to the 5' and 3' sequences of the gene:

The 5' primer has the sequence TGT AAT ACG ACT CAC TAT AGG GAT CCC GCC ATG GAG GCC ACG GCT TAT GC (SEQ ID NO:7) and contains a BamH1 restriction enzyme site (in bold) and 17 nucleotide nucleotide sequence complementary to the 5' sequence of VEGF2 (nt. 150-166).

The 3' primer has the sequence GATC TCT AGA TTA GCT CAT TTG TGG TCT (SEQ ID NO:8) and contains the cleavage site for the restriction enzyme XbaI and 18 nucleotides complementary to the 3' sequence of VEGF2, including the stop codon and 15 nt sequence before stop codon.

The amplified sequences were isolated from a 1% agarose gel using a commercially available kit ("Geneclean," BIO 101, Inc., La Jolla, Calif.). The fragment was then digested with the endonuclease BamH1 and XbaI and then purified again on a 1% agarose gel. This fragment was ligated to pAcGP67A baculovirus transfer vector (PHarmingen) at the BamH1 and XbaI sites. Through this ligation, VEGF2 cDNA was cloned in frame with the signal sequence of baculovirus gp67 gene and was located at the 3' end of the signal sequence in the vector. This is designated pAcGP67A-VEGF2.

To clone VEGF2 with the signal sequence of gp67 gene to the pRG1 vector for expression, VEGF2 with the signal sequence and some upstream sequence were excised from the pAcGP67A-VEGF2 plasmid at the Xho restriction endonuclease site located upstream of the VEGF2 cDNA and at the XbaI restriction endonuclease site by XhoI and XbaI restriction enzyme. This fragment was separated from the rest of vector on a 1% agarose gel and was purified using "Geneclean" kit. It was designated F2.

The PRG1 vector (modification of pVL941 vector) is used for the expression of the VEGF2 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamH1, SmaI, XbaI, BglII and Asp718. A site for restriction endonuclease Xho1 is located upstream of BamH1 site. The sequence between Xho1 and BamHI is the same as that in PAcGp67A (static on tape) vector. The polyadenylation site of the simian virus (SV)40 is used for efficient polyadenylation. For an easy selection of recombinant virus the beta-galactosidase gene from E. coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170: 31-39).

The plasmid was digested with the restriction enzymes XboI and XbaI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E. coli HB101 cells were then transformed and bacteria identified that contained the plasmid (pBac gp67-VEGF2) with the VEGF2 gene using the enzymes BamH1 and XbaI. The sequence of the cloned fragment was confirmed by DNA sequencing.

5 µg of the plasmid pBac gp67-VEGF2 was cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413-7417 (1987)).

1 µg of BaculoGold™ virus DNA and 5 µg of the plasmid pBac gp67-VEGF2 were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9-10).

Four days after the serial dilution, the virus was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-gp67-VEGF2 at a multiplicity of infection (MOI) of 1. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

Figure 4:
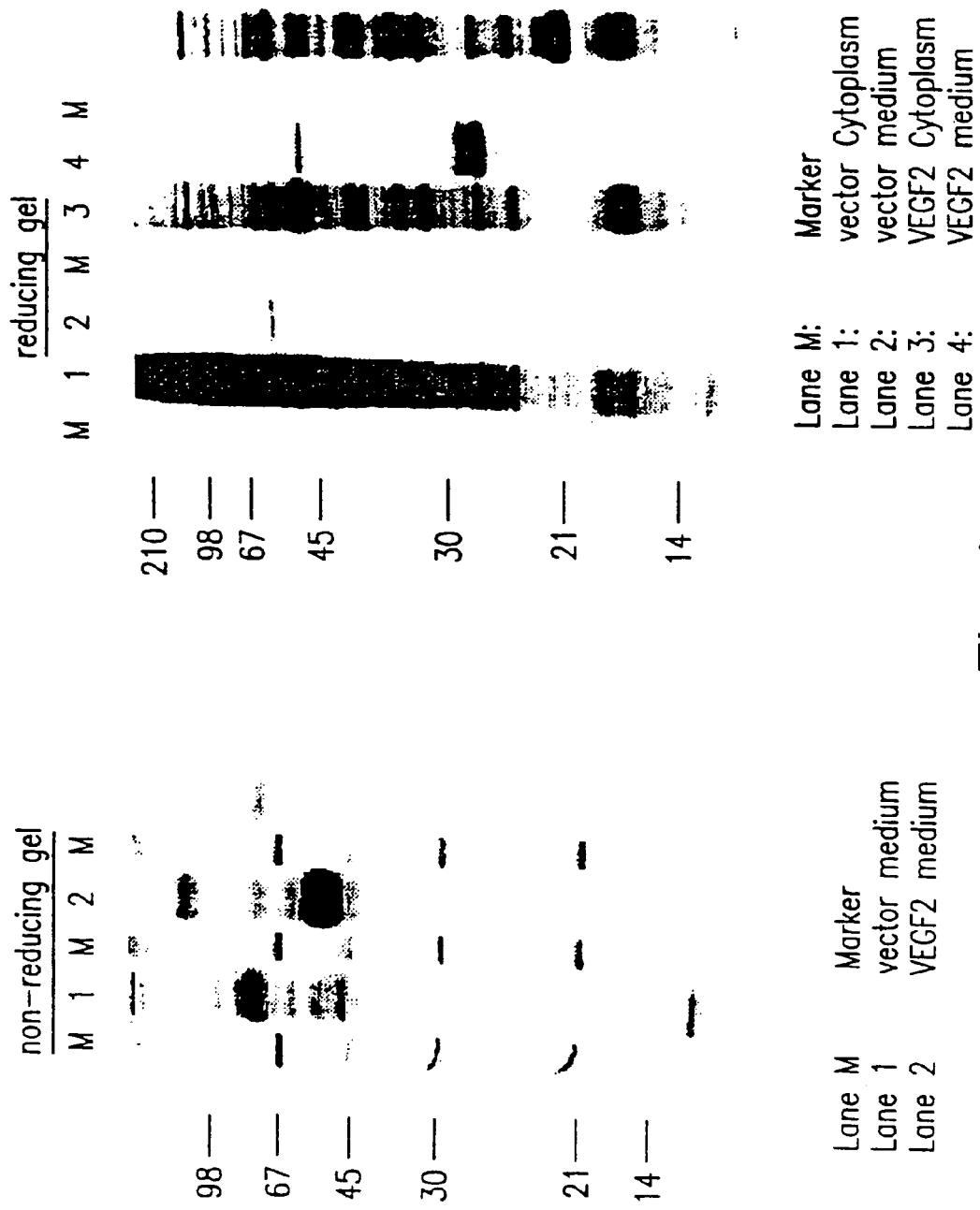
FIG. 4. VEGF2 polypeptide is expressed in a baculovirus system consisting of Sf9 cells. Protein from the medium and cytoplasm of cells were analyzed by SDS-PAGE under reducing and non-reducing conditions.
Figure 5:
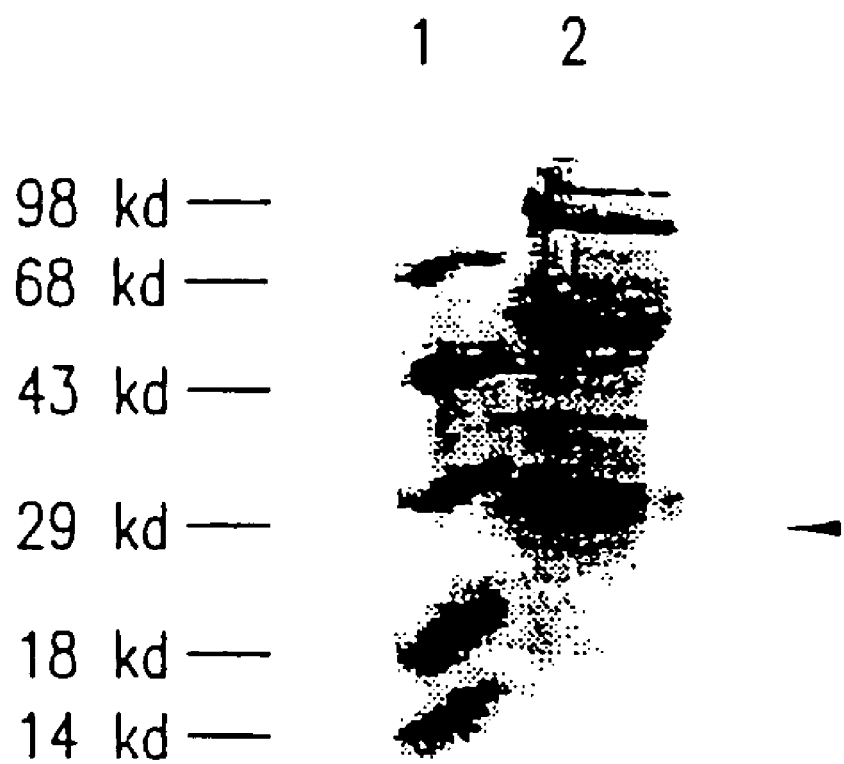
FIG. 5. The medium from Sf9 cells infected with a nucleic acid sequence of the present invention was precipitated and the resuspended precipitate was analyzed by SDS-PAGE and was stained with coomassie brilliant blue.

Protein from the medium and cytoplasm of the Sf9 cells was analyzed by SDS-PAGE under reducing and non-reducing conditions. See FIG. 4. The medium was dialyzed against 50 mM MES, pH 5.8. Precpitates were obtained after dialysis and resuspended in 100 mM NaCitrate, pH 5.0. The resuspended precipitate was analyzed again by SDS-PAGE and was stained with Coomassie Brilliant Blue. See FIG. 5.

Figure 6:
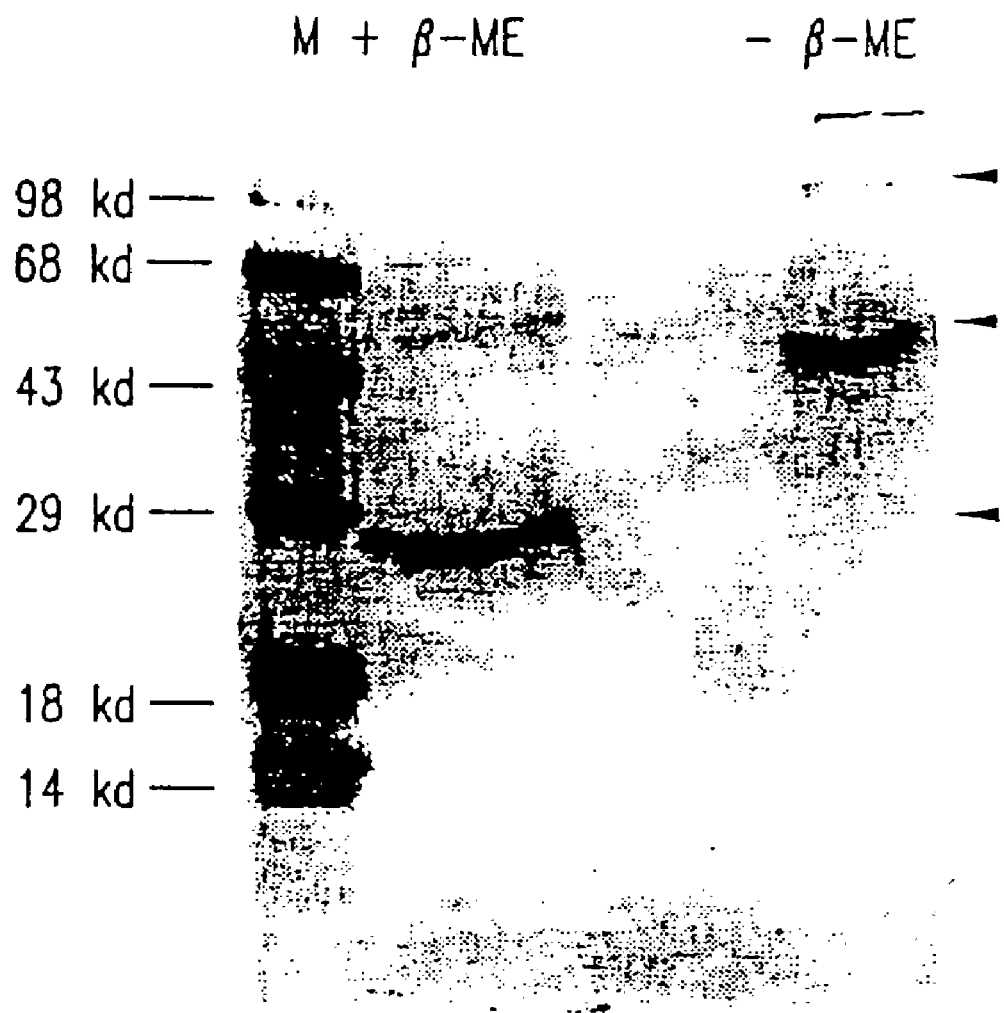
FIG. 6. VEGF2 was purified from the medium supernatant and analyzed by SDS-PAGE in the presence or absence of the reducing agent β-mercaptoethanol and stained by coomassie brilliant blue.
Figure 7:
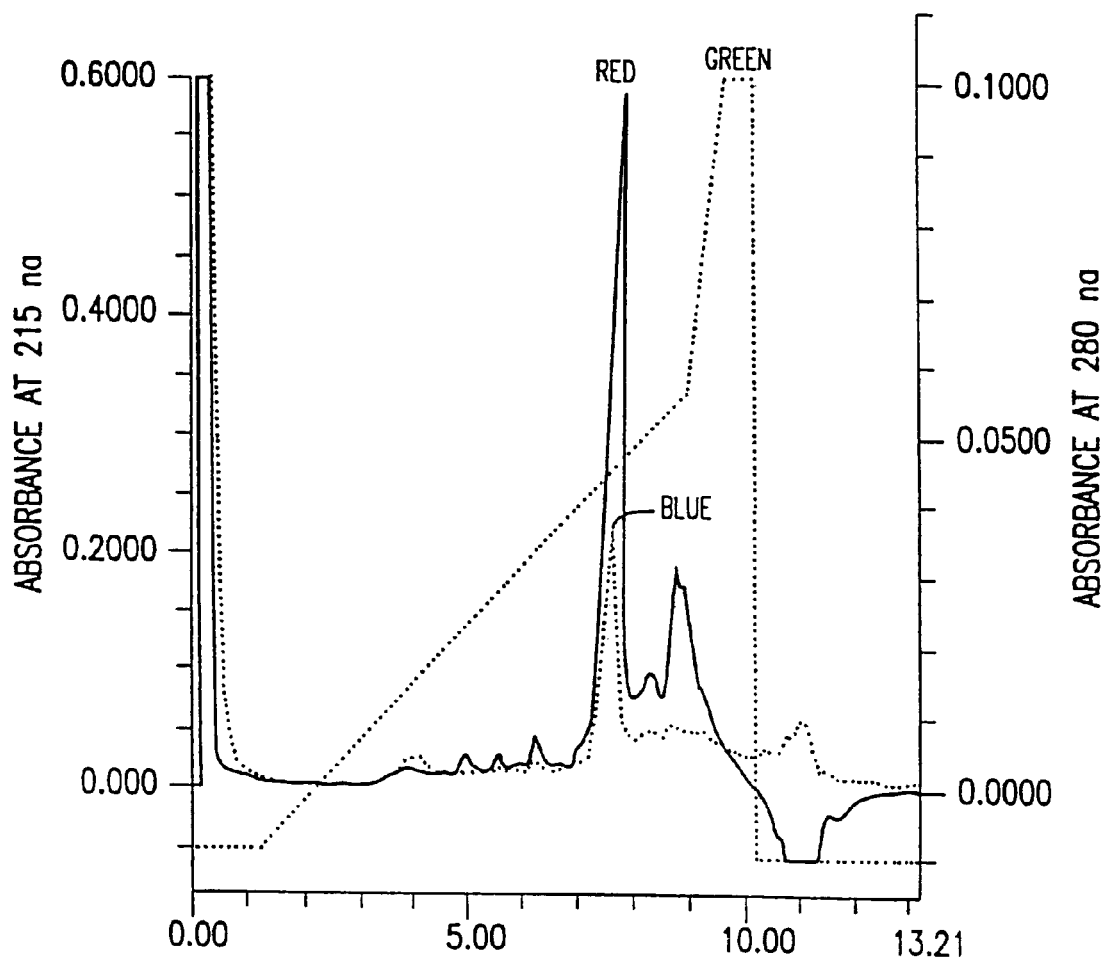
FIG. 7. Reverse phase HPLC analysis of purified VEGF2 using a RP-300 column (0.21×3 cm, Applied Biosystems, Inc.). The column was equilibrated with 0.1% trifluoroacetic acid (Solvent A) and the proteins eluted with a 7.5 min gradient from 0 to 60% Solvent B, composed of acetonitrile containing 0.07% TFA. The protein elution was monitored by absorbance at 215 nm (Red line) and 280 nm (Blue line). The percentage of Solvent B is shown by Green line.

The medium supernatant was also diluted 1:10 in 50 mM MES, pH 5.8 and applied to an SP-650M column (1.0×6.6 cm, Toyopearl) at a flow rate of 1 ml/min. Protein was eluted with step gradients at 200, 300 and 500 mM NaCl. The VEGF2 was obtained using the elution at 500 mM. The eluate was analyzed by SDS-PAGE in the presence or absence of reducing agent, β-mercaptoethanol and stained by Coommassie Brilliant Blue. See FIG. 6.

EXAMPLE 3

Expression of Recombinant VEGF2 in COS Cells

The expression of plasmid, VEGF2-HA is derived from a vector pcDNAI/Amp (Invitrogen) containing: 1) SV40 origin of replication, 2) ampicillin resistance gene, 3) E. coli replication origin, 4) CMV promoter followed by a polylinker region, an SV40 intron and polyadenylation site. A DNA fragment encoding the entire VEGF2 precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding VEGF2, ATCC No. 97149, was constructed by PCR using two primers: the 5' primer (CGC GGA TCC ATG ACT GTA CTC TAC CCA) (SEQ ID NO:9) contains a BamH1 site followed by 18 nucleotides of VEGF2 coding sequence starting from the initiation codon; the 3' sequence (CGC TCT AGA TCA AGC GTA GTC TGG GAC GTC GTA TGG GTA CTC GAG GCT CAT TTG TGG TCT 3') (SEQ ID NO:10) contains complementary sequences to an XbaI site, HA tag, XhoI site, and the last 15 nucleotides of the VEGF2 coding sequence (not including the stop codon). Therefore, the PCR product contains a BamHI site, coding sequence followed by an XhoI restriction endonuclease site and HA tag fused in frame, a translation termination stop codon next to the HA tag, and an XbaI site. The PCR amplified DNA fragment and the vector, pcDNAI/Amp, were digested with BamH1 and XbaI restriction enzyme and ligated. The ligation mixture was transformed into E. coli strain SURE (Stratagene Cloning Systems, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant VEGF2, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the VEGF2-HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Proteins precipitated were analyzed on 15% SDS-PAGE gels.

EXAMPLE 4

The Effect of Partially-Purified VEGF2 Protein on the Growth of Vascular Endothelial Cells On day 1, human umbilical vein endothelial cells (HUVEC) were seeded at 2–5×10⁴ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium was replaced with M199 containing 10% FBS, 8 units/ml heparin. VEGF2 protein of SEQ ID NO. 2 minus the initial 45 amino acid residues, (VEGF) and basic FGF (bFGF) were added, at the concentration shown. On days 4 & 6, the

EXAMPLE 5

The Effect of Purified VEGF2 Protein on the Growth of Vascular Endothelial Cells On day 1, human umbilical vein endothelial cells (HU-VEC) were seeded at 2–5×10$^4$ cells/35 mm dish density in M199 medium containing 4% fetal bovine serum (FBS), 16 units/ml heparin, 50 units/ml endothelial cell growth supplements (ECGS, Biotechnique, Inc.). On day 2, the medium was replaced with M199 containing 10% FBS, 8 units/ml heparin. Purified VEGF2 protein of SEQ ID No. 2 minus initial 45 amino acid residues was added to the medium at this point. On days 4 & 6, the medium was replaced with fresh medium and supplements. On day 8, cell number was determined with a Coulter Counter (See FIG. 9).

EXAMPLE 6

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37 C for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219-25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed:

1. An isolated antibody or fragment thereof selected from the group consisting of:
   (I) an isolated antibody or fragment thereof that specifically binds a protein selected from the group consisting of:
      (a) a protein consisting of amino acid residues −46 to 373 of SEQ ID NO:2;
      (b) a protein consisting of amino acid residues −23 to 373 of SEQ ID NO:2;
      (c) a protein consisting of amino acid residues 1 to 373 of SEQ ID NO:2;
      (d) a protein consisting of amino acid residues 24 to 373 of SEQ ID NO:2;
      (e) a protein consisting of a fragment of SEQ ID NO:2, wherein said fragment comprises at least 30 contiguous amino acid residues of SEQ ID NO:2;
      (f) a protein consisting of a fragment of SEQ ID NO:2, wherein said fragment comprises at least 50 contiguous amino acid residues of SEQ ID NO:2;
      (g) a protein consisting of the full-length polypeptide encoded by the cDNA contained in ATCC Deposit Number 97149;
      (h) a purified protein produced by expressing a polypeptide encoded by the cDNA contained in ATCC Deposit No. 97149 from a host cell;
      (i) a protein consisting of a fragment of the polypeptide encoded by the cDNA contained in ATCC Deposit Number 97149, wherein said fragment comprises at least 30 contiguous amino acid residues of the polypeptide encoded by the cDNA contained in ATCC Deposit Number 97149; and
      (j) a protein consisting of a fragment of the polypeptide encoded by the cDNA contained in ATCC Deposit Number 97149, wherein said fragment comprises at least 50 contiguous amino acid residues of the polypeptide encoded by the cDNA contained in ATCC Deposit Number 97149; and
   (II) an isolated antibody or fragment thereof obtained from an animal that has been immunized with a protein selected from (a)-(j); wherein said antibody or fragment thereof specifically binds to said amino acid sequence.

2. The antibody or fragment thereof of claim 1 that specifically binds protein (a).

3. The antibody or fragment thereof of claim 1 that specifically binds protein (g).

4. The antibody or fragment thereof of claim 2 wherein said protein bound by said antibody or fragment thereof is glycosylated.

5. The antibody or fragment thereof of claim 2 which is a polyclonal antibody.

6. The antibody or fragment thereof of claim 2 which is a monoclonal antibody.

7. The antibody or fragment thereof of claim 2 which is selected from the group consisting of:
   (a) a chimeric antibody;
   (b) a single chain antibody; and
   (c) a Fab fragment.

8. The antibody or fragment thereof of claim 2 which is labeled.

9. The antibody or fragment thereof of claim 8 wherein the label is selected from the group consisting of:
   (a) an enzyme; and
   (b) a fluorescent label.

10. The antibody or fragment thereof of claim 2 wherein said antibody specifically binds to said protein in a Western blot or an ELISA.

11. An isolated cell that produces the antibody or fragment thereof of claim 2.

12. A hybridoma that produces the antibody or fragment thereof of claim 2.

13. A method of detecting VEGF-2 protein in a biological sample comprising:
   (a) contacting the biological sample with the antibody or fragment thereof of claim 2; and
   (b) detecting the VEGF-2 protein in the biological sample.

14. A method of inhibiting angiogenesis in a patient comprising administering to the patient a therapeutically effective amount of the antibody of claim 1.

15. A method of inhibiting neovascularization in a patient comprising administering to the patient a therapeutically effective amount of the antibody of claim 1.

16. A method of inhibiting a tumor in a patient comprising administering to the patient a therapeutically effective amount of the antibody of claim 1.

17. A method of inhibiting diabetic retinopathy in a patient comprising administering to the patient a therapeutically effective amount of the antibody of claim 1.

18. A method of inhibiting psoriasis in a patient comprising administering to the patient a therapeutically effective amount of the antibody of claim 1.

19. A method of inhibiting rheumatoid arthritis in a patient comprising administering to the patient a therapeutically effective amount of the the antibody of claim 1.

20. An isolated antibody which binds to a purified protein produced by expressing a polypeptide encoded by the cDNA contained in ATCC Deposit No. 97149 from a host cell.

21. A composition comprising an antibody according to claim 20, in a carrier.

22. An antibody according to claim 20 that is a monoclonal antibody.

23. An antibody according to claim 20, further comprising a label.

24. An isolated antibody which binds to a protein produced by a method comprising:
   (a) expressing a polypeptide comprising the amino acid sequence of SEQ ID NO:2 from a mammalian host cell; and
   (b) recovering the protein.

25. The antibody of claim 24, wherein the mammalian host cell comprises a CHO or COS host cell.

26. A composition comprising an antibody according to claim 24, in a carrier.

27. An antibody according to claim 24 that is a monoclonal antibody.

28. An antibody according to claim 24, further comprising a label.

29. An isolated monoclonal antibody that specifically binds to amino acid residues −46 to 111 or −26 to 111 of SEQ ID NO:2.

30. The monoclonal antibody of claim 29, wherein the antibody neutralizes a biological activity of VEGF2.

31. The monoclonal antibody of claim 30, wherein the biological activity of VEGF2 is promoting neovascularization, vascular permeability, or vascular endothelial cell growth in a mammal.

32. The monoclonal antibody of claim 30, wherein the antibody is a humanized antibody.

33. The monoclonal antibody of claim 30, wherein the antibody is a chimeric antibody.

34. A composition comprising a monoclonal antibody of claim 30 with a pharmaceutically acceptable carrier.

35. An isolated monoclonal antibody or fragment thereof that specifically binds a protein selected from the group consisting of:
   (a) a protein consisting of amino acid residues −46 to 85 of SEQ ID NO:2;
   (b) a protein consisting of amino acid residues −46 to 108 of SEQ ID NO:2;
   (c) a protein consisting of amino acid residues −46 to 121 of SEQ ID NO:2;
   (d) a protein consisting of amino acid residues −46 to 165 of SEQ ID NO:2;
   (e) a protein consisting of amino acid residues −23 to 85 of SEQ ID NO: 2;
   (f) a protein consisting of amino acid residues −23 to 108 of SEQ ID NO:2;
   (g) a protein consisting of amino acid residues −23 to 121 of SEQ ID NO:2; and
   (h) a protein consisting of amino acid residues −23 to 165 of SEQ ID NO:2.

36. The isolated antibody or fragment thereof of claim 35 that specifically binds protein (a).

37. The isolated antibody or fragment thereof of claim 35 that specifically binds protein (b).

38. The isolated antibody or fragment thereof of claim 35 that specifically binds protein (c).

39. The isolated antibody or fragment thereof of claim 35 that specifically binds protein (d).

40. The isolated antibody or fragment thereof of claim 35 that specifically binds protein (e).

41. The isolated antibody or fragment thereof of claim 35 that specifically binds protein (f).

42. The isolated antibody or fragment thereof of claim 35 that specifically binds protein (g).

43. The isolated antibody or fragment thereof of claim 35 that specifically binds protein (h).

44. The isolated monoclonal antibody of claim 35, wherein the antibody neutralizes a biological activity of human VEGF2.

45. The isolated antibody or fragment thereof of claim 44 which is a humanized antibody.

46. The isolated antibody or fragment thereof of claim 44 which is a chimeric antibody.

47. The isolated antibody or fragment thereof of claim 44 wherein the biological activity of human VEGF2 is promoting neovascularization, vascular permeability, or vascular endothelial cell growth in a mammal.

48. A composition comprising the antibody or fragment thereof of claim 44 with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,576,189 B2 | Page 1 of 1 |
| APPLICATION NO. | : 11/211724 | |
| DATED | : August 18, 2009 | |
| INVENTOR(S) | : Rosan et al. | |

It is certified that error appears in the above-identified patent and that said Letters Patent is hereby corrected as shown below:

On the cover page, item [*] Notice: Subject to any disclaimer, the term of this patent is extended or adjusted under 35 USC 154(b) by 53 days Delete the phrase "by 53 days" and insert -- by 130 days --

Signed and Sealed this

Eighth Day of June, 2010

David J. Kappos
*Director of the United States Patent and Trademark Office*